US009514531B2

(12) United States Patent
Chono

(10) Patent No.: US 9,514,531 B2
(45) Date of Patent: Dec. 6, 2016

(54) MEDICAL IMAGE DIAGNOSTIC DEVICE AND METHOD FOR SETTING REGION OF INTEREST THEREFOR

(71) Applicant: HITACHI ALOKA MEDICAL, LTD., Mitaka-shi, Tokyo (JP)

(72) Inventor: Tomoaki Chono, Mitaka (JP)

(73) Assignee: Hitachi, Ltd., Tokyo (JP)

(*) Notice: Subject to any disclaimer, the term of this patent is extended or adjusted under 35 U.S.C. 154(b) by 211 days.

(21) Appl. No.: 14/373,837

(22) PCT Filed: Jan. 29, 2013

(86) PCT No.: PCT/JP2013/051926
§ 371 (c)(1),
(2) Date: Jul. 22, 2014

(87) PCT Pub. No.: WO2013/115194
PCT Pub. Date: Aug. 8, 2013

(65) Prior Publication Data
US 2014/0369564 A1 Dec. 18, 2014

(30) Foreign Application Priority Data

Feb. 2, 2012 (JP) ................................ 2012-021070

(51) Int. Cl.
G06T 7/00 (2006.01)
A61B 8/00 (2006.01)
(Continued)

(52) U.S. Cl.
CPC ............ *G06T 7/0012* (2013.01); *A61B 6/469* (2013.01); *A61B 8/0883* (2013.01); *A61B 8/488* (2013.01);
(Continued)

(58) Field of Classification Search
CPC ........ G06T 7/0012; G06T 7/0081; G06T 9/00; A61B 5/7232; A61B 6/469; A61B 8/469
See application file for complete search history.

(56) References Cited

U.S. PATENT DOCUMENTS

2003/0081848 A1  5/2003  Wada ............................ 382/240
2005/0238216 A1 10/2005  Yoden ........................... 382/128
(Continued)

FOREIGN PATENT DOCUMENTS

CN    101346982 A    1/2009    ............... H04N 1/41
JP    2005-218796 A  8/2005    ............... A61B 8/08
(Continued)

OTHER PUBLICATIONS

Office Action dated Aug. 31, 2015, issued in counterpart Chinese Patent Application No. 201380007856.5, w/English translation (18 pages).
(Continued)

Primary Examiner — Andrew W Johns
(74) Attorney, Agent, or Firm — Westerman, Hattori, Daniels & Adrian, LLP

(57) ABSTRACT

The present invention comprises: capturing a medical image of a subject by an image-capturing unit; generating compressed image data by compressing on the basis of a plurality of pixels of uncompressed image data, where the uncompressed image data is image data of the captured medical image of the subject, by an image data compression unit; setting a search range of the compressed image data and also setting a search range of the uncompressed image data, by a search range setting unit; and setting a region of interest for the medical image on the basis of the search range of the uncompressed image data and the search range of the compressed image data, by a region-of-interest setting unit.

15 Claims, 17 Drawing Sheets

(51) Int. Cl.
    *A61B 6/00*    (2006.01)
    *A61B 8/08*    (2006.01)
    *G06T 9/00*    (2006.01)

(52) U.S. Cl.
    CPC .............. *A61B 8/5207* (2013.01); *G06T 9/00* (2013.01); *A61B 8/486* (2013.01); *A61B 8/56* (2013.01); *G06T 2207/10132* (2013.01); *G06T 2207/30004* (2013.01)

(56) References Cited

U.S. PATENT DOCUMENTS

| | | | |
|---|---|---|---|
| 2008/0069417 A1 | 3/2008 | Kimura | 382/131 |
| 2009/0281425 A1 | 11/2009 | Sasahara et al. | 600/443 |
| 2011/0243470 A1 | 10/2011 | Noguchi | 382/239 |
| 2012/0014608 A1 | 1/2012 | Watanabe | 382/195 |
| 2012/0300903 A1 | 11/2012 | Yao et al. | 378/62 |
| 2014/0193768 A1* | 7/2014 | Ogawa et al. | A61B 6/5241 433/29 |

FOREIGN PATENT DOCUMENTS

| | | | |
|---|---|---|---|
| JP | 2005-287927 A | 10/2005 | A61B 5/00 |
| JP | 2007-37864 A | 2/2007 | A61B 6/00 |
| JP | 2008-586 A | 1/2008 | A61B 5/055 |
| JP | 2010-136779 A | 6/2010 | A61B 6/00 |
| JP | 2011-217130 A | 10/2011 | H04N 7/26 |
| JP | 2012-21904 A | 2/2012 | G01N 21/27 |
| KR | 10-2010-0095833 A | 9/2010 | H04N 7/24 |
| TW | 200420115 A | 10/2004 | H04N 1/41 |

OTHER PUBLICATIONS

Extended European Search Report dated May 15, 2015, issued in corresponding Patent Application No. 13743588.9 (6 pages).
Notification Concerning Transmittal of International Preliminary Report on Patentability (PCT/IB/326) of International Application No. PCT/JP2013/051926, mailing date of Aug. 14, 2014, with Forms PCT/IB/373, PCT/ISA/237.
International Search Report dated Feb. 26, 2013, issued in corresponding application No. PCT/JP2013/051926.

* cited by examiner

MEDICAL IMAGE DIAGNOSTIC DEVICE AND METHOD FOR SETTING REGION OF INTEREST THEREFOR

TECHNICAL FIELD

The present invention relates to a medical image diagnostic device and particularly relates to a medical image diagnostic device that sets a region of interest including a characteristic part or a measurement position, and to a method for setting a region of interest therefor.

BACKGROUND ART

The information of physical quantities of living tissues of subjects is information which is measured by a medical image diagnostic device and is important for diagnosing the levels of pathological changes. The information of the physical quantities consists of the length, area, volume, movement, etc. of the living tissues of the subject.

In conventional techniques, an examiner uses an input device (for example, a mouse or a trackball) of a medical image diagnostic device to manually set a position or region (region of interest), which is desired to be measured, within a desired region on a medical image displayed on a screen of a display unit.

Since the manual setting of the region of interest is carried out by a subjective view of the examiner, under manual setting of the region of interest, not all examiners would always set the same region of interest under a given set of conditions.

Therefore, a method is proposed in Patent Document 1 in which the medical image diagnostic device searches for the contour of an organ region within the entire image data of medical images, sets a region of interest in accordance with, for example, template matching based on the search result thereof, and extracts the contour of a left-ventricle inner membrane based on the position of an annulus part of the heart.

CITATION LIST

Patent Literature

PATENT DOCUMENT 1: Japanese Patent Laid-Open Publication No. 2005-218796

SUMMARY OF INVENTION

Technical Problem

However, only with the template matching with respect to the entire image data of the medical images of Patent Document 1, search time reduction for setting the region of interest is conceived to be an unsolved problem in a case in which the region of interest is set in real time.

Therefore, an object of the present invention is to provide a medical image diagnostic device that achieves search time reduction for setting a region of interest in a case in which the region of interest is set in real time, and a method for setting a region of interest therefor.

Solution to Problem

The present invention includes: capturing a medical image of a subject by an image capturing unit; using image data of the captured medical image of the subject as uncompressed image data and generating compressed image data by compression based on a plurality of pixels of the uncompressed image data by an image-data compression unit; setting a search range of the compressed image data and setting a search range of the uncompressed image data by the search-range setting unit; and setting a region of interest within the medical image based on the search range of the uncompressed image data and the search range of the compressed image data by a region-of-interest setting unit.

Advantageous Effect of Invention

According to the present invention, a medical image diagnostic device achieves search time reduction for setting region of interest in a case in which the region of interest is set in real time by setting the region of interest by using set search ranges of image data before and after compression and a method for setting the region of interest therefor.

DESCRIPTION OF EMBODIMENTS

First Embodiment

Figure 1:
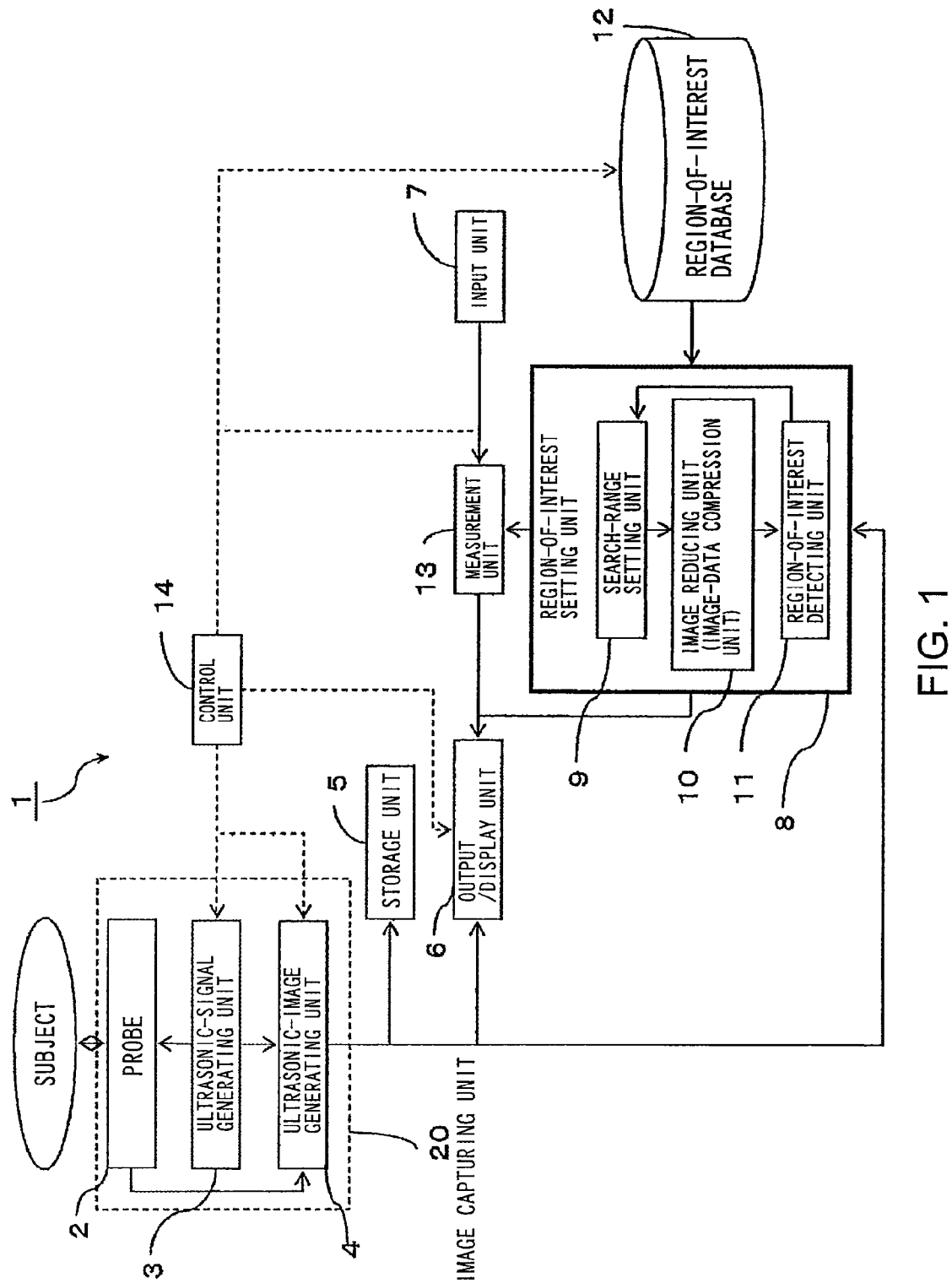
FIG. 1 is a block diagram exemplifying an ultrasonic diagnostic device (medical image diagnostic device) of a first embodiment of the present invention.

Hereinafter, a medical image diagnostic device of a first embodiment of the present invention will be explained by using an ultrasonic diagnostic device, which is an example of the medical image diagnostic device. FIG. 1 is a block diagram exemplifying an ultrasonic diagnostic device (medical image diagnostic device) 1 as an example of an image capturing unit 20 of the first embodiment of the present invention, which captures medical images of subjects.

The ultrasonic diagnostic device 1 shown in FIG. 1 is provided with: a probe 2; an ultrasonic-signal generating unit 3; an ultrasonic-image generating unit 4; a storage unit 5; an output/display unit 6 an input unit 7; a region-of-interest setting unit 8; a region-of-interest database 12 including a reference-coordinate storage unit; a measurement unit 13; and a control unit 14. The region-of-interest setting unit 8 includes a search-range setting unit 9, an image reducing unit (image-data compression unit) 10, and a region-of-interest detecting unit 11.

The probe 2 is a device which transmits ultrasonic waves from a vibrator to a target tissue and receives them and carries out a scanning method of, for example, a linear type, a convex type, or a sector type. The ultrasonic-signal generating unit 3 transmits electrically-converted ultrasonic signals to the probe 2. The ultrasonic-signal generating unit 3 receives the information of the power and timing of transmission/reception from the control unit 14; as a result, the transmission/reception of ultrasonic waves via the probe 2 is controlled so that desired ultrasonic waves are generated.

The ultrasonic-image generating unit 4 generates ultrasonic images based on image-capture setting (for example, a scanning range of ultrasonic beams, gain setting, etc.) of the device from the ultrasonic signals generated from the ultrasonic-signal generating unit 3. The ultrasonic images are constantly updated in accordance with a frame rate determined by the image-capture setting and are displayed as video images on a screen of the ultrasonic diagnostic device by the output/display unit 6.

The storage unit 5 stores generated ultrasonic signals, ultrasonic images (medical images), and signal data and image data obtained from subjects such as electrocardiograms. Moreover, the storage unit 5 stores programs for operating various systems constituting the ultrasonic diagnostic device 1. For example, the storage unit 5 is a storage medium such as a semiconductor memory, a hard disk, or an optical disk. Furthermore, the storage unit 5 may be an external storage medium used through a network.

The output/display unit 6 displays the ultrasonic images (medical images) on the screen of the device, displays the regions of interest set by the region-of-interest setting unit 8 so that the regions are superimposed on the ultrasonic images, and displays measurement values of living-body tissues, which have been measured by the measurement unit 13, on an ultrasonic screen. The output/display unit 6 stores the ultrasonic images (medical images) and the measurement values and outputs the ultrasonic images (medical images) and the measurement values as measurement reports.

The input unit 7 is an interface which carries out various operations of the ultrasonic diagnostic device 1. Particularly, in the present embodiment, the input unit 7 is used for selecting an item, which is desired to be measured by an examiner, from a measurement menu. For example, the input unit 7 is an input device such as a keyboard, a trackball, a switch, or a dial. Moreover, the input unit 7 may include a sound inputting function.

The region-of-interest setting unit 8 sets regions of interest for measurement based on measurement items set by the input unit 7. The region-of-interest setting unit 8 functions so as to set a search range based on region-of-interest set values (for example, a reference coordinate serving as a reference of the position of the region of interest) stored in advance in the region-of-interest database 12, recursively set regions of interest on a plurality of pieces of image data having different reduction ratios (compression ratios), and improve the accuracy of setting of the regions of interest including characteristic parts while improving the space resolution of the set positions of the regions of interest. In order to implement this function, the region-of-interest setting unit 8 includes the search-range setting unit 9, the image reducing unit (image-data compression unit) 10, and the region-of-interest setting unit 11, and the operations of the search-range setting unit 9, the image reducing unit 10, and the region-of-interest setting unit 11 are repeatedly carried out with respect to the image data while changing the reduction ratios (compression ratios) of the image data. The operations of the search-range setting unit 9, the image reducing unit 10, and the region-of-interest setting unit 11 are repeatedly carried out from the image data having low (high) reduction ratios (compression ratios) to the image data having high (low) reduction ratios (compression ratios).

The search-range setting unit 9 sets a search range of the image data. The search-range setting unit 9 determines the search range for carrying out template matching in the image data. An initial value (for example, the reference coordinate serving as the reference of the position of the region of interest) of the search range used for determining a first search range (initial search range) is read from the region-of-interest database 12 and used. Moreover, the search-range setting unit 9 changes the search range in accordance with the reduction ratio (compression ratio) of the image. Furthermore, the search-range setting unit 9 subjects the image data to a contour extracting process in order to set the region of interest.

The image reducing unit (image-data compression unit) 10 carries out compression of the image data based on a plurality of pixels and changes the compression ratio of the image data. The image reducing unit (image-data compression unit) 10 generates a plurality of pieces of reduced image data (compressed image data) having different reduction ratios (compression ratios). Existing methods such as a nearest neighbor method and a bicubic method are utilized as the method of reduction (the method of compression).

The region-of-interest setting unit 11 sets a region of interest including a characteristic part (for example, an annulus part of the heart) in the search range set by the search-range setting unit 9. By using pattern classification (for example, template matching), the region-of-interest setting unit 11 sets a position which has the highest possibility of being the region of interest within the search range. The region of interest is set in the search range, which is set by the search-range setting unit 9 on a reduced image (compressed image) generated by the image reducing unit (image-data compression unit) 10. Examples of the method of the template matching include a SAD (Sum of Absolute Difference) method, a method based on main-component analysis such as subspace method, and a method by Boosting. Also, examples of pattern recognition include a k-nearest neighbor classification method, a subspace method, a method by optimization of discrimination function, a method by a decision tree, and a method by a neural network.

The region-of-interest database 12 includes the reference-coordinate storage unit, which stores the reference coordinates serving as the references of the positions of the regions of interest. For example, the region-of-interest database 12 stores the coordinate data of regions of interest or characteristic parts based on a plurality of pieces of past sample data as reference coordinates. Moreover, the region-of-interest database 12 stores template data of the regions of interest based on the plurality of pieces of past sample data. If the region-of-interest setting unit 11 uses the SAD method, the correlations with the template data may be calculated; if the region-of-interest setting unit 11 uses the subspace method or Boosting, learning results may be stored in the region-of-interest database 12 and utilized in matching operations.

The measurement unit 13 calculates measurement values about the measurement items set by the input unit 7. The present embodiment will be explained by mainly taking the measurement of the heart as an example, but can be also utilized in measurement of vessels or tumors other than the heart. For example, the size and movement of an organ is measured. The measurement values are displayed on the screen of the device together with the ultrasonic images (medical images) by the output/display unit 6.

The control unit 14 controls a whole system and controls the synchronization of a series of processes of the region-of-interest setting unit 8, the region-of-interest database 12, the measurement unit 13, and the output/display unit 6. For example, a control device such as a CPU is used as the control unit 14.

Then, operations of the ultrasonic diagnostic device (medical image diagnostic device) 1 according to the present embodiment will be explained. The present embodiment explains a case in which physical quantities such as the volume and speed of the heart are measured about the setting of a region of interest including a characteristic part of the heart.

Figure 2:
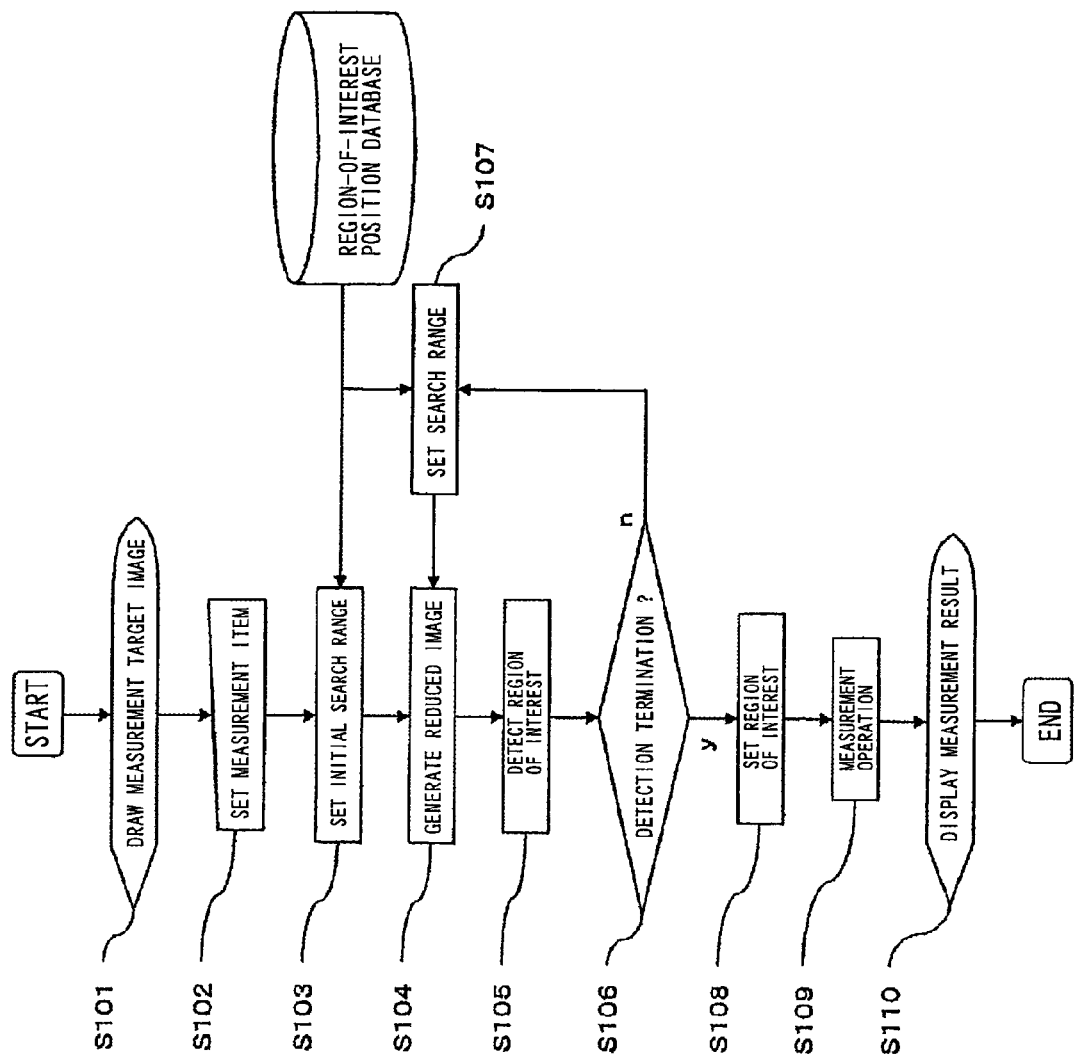
FIG. 2 is a flow chart explaining operations of the medical image diagnostic device according to the first embodiment of the present invention.

FIG. 2 is a flow chart explaining the operations of the ultrasonic diagnostic device 1 according to the present embodiment. As shown in FIG. 2, the present embodiment explains a method for setting a region of interest in accordance with a measurement item set by an examiner, which is a method for improving the accuracy of setting a region of interest including a characteristic part while improving the space resolution of the set position of the region of interest by determining a search range of template matching based on the reference coordinate stored in the region-of-interest database 12 and recursively setting regions of interest on a plurality of reduced images (compressed images).

Figure 3:
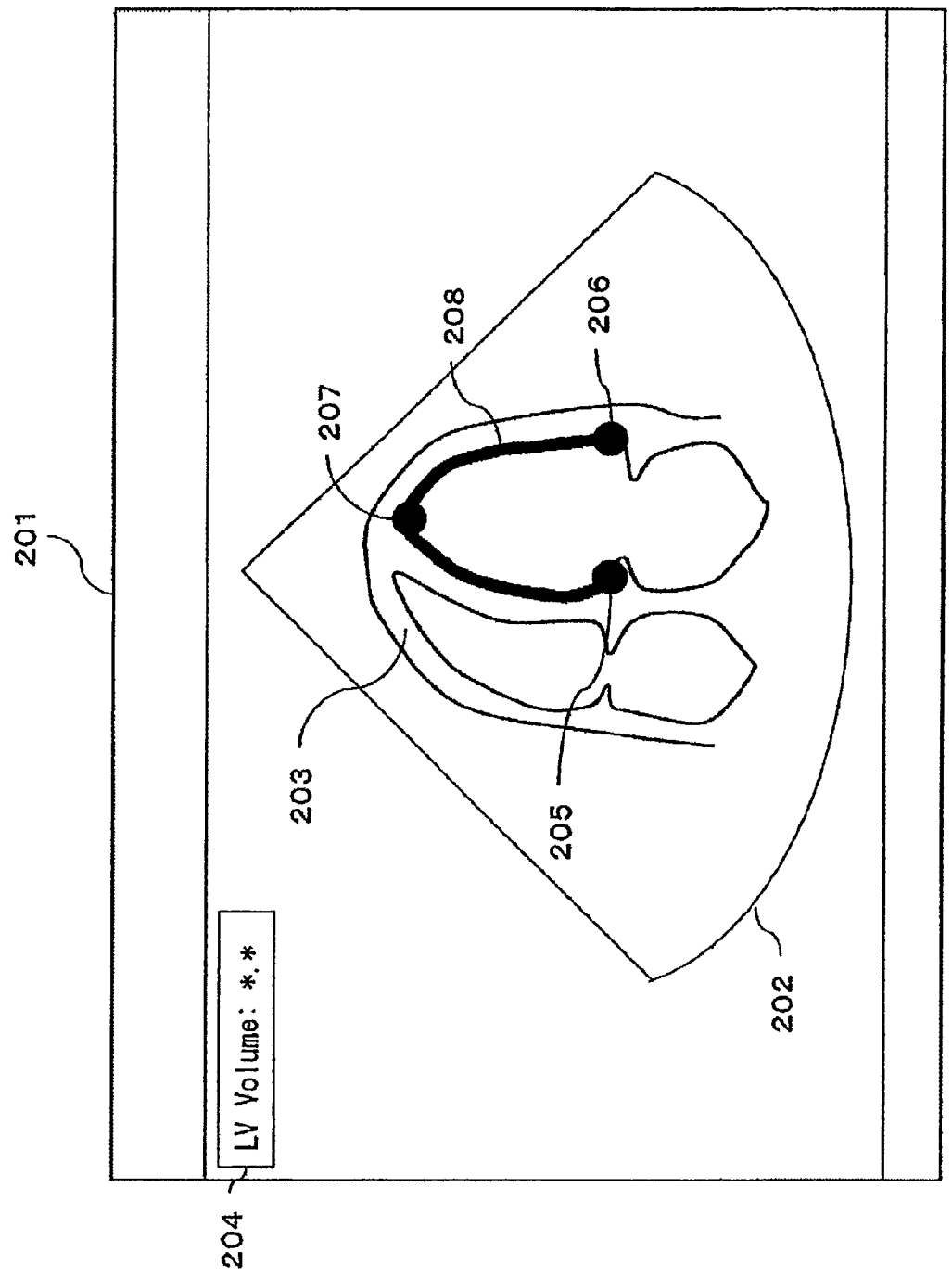
FIG. 3 is a drawing showing an example of image data of a living-body tissue displayed by an output/display unit.

As shown in FIG. 2, the output/display unit 6 displays an image on which a living-body tissue serving as a target is drawn on a display screen (step S101). For example, as shown in FIG. 3, if measurement of the left ventricle is an object, the output/display unit 6 displays a cardiac-apex 4-chamber view 202 on the display screen 201.

The input unit 7 sets a measurement item (step S102). For example, as shown by a measurement item (measurement-value field) 204 of FIG. 3, the input unit 7 sets LV (Left Ventricle) Volume (left-ventricle volume) as the measurement item. In a case in which a Modified Simpson method is used, extraction of a contour line 208 of the left ventricle is required in order to measure the left-ventricle volume. In a case in which the left-ventricle contour line is to be extracted from an ultrasonic image (medical image), the accuracy of contour extraction of extracting the contour of a left-ventricle inner membrane is improved by setting a region of interest including characteristic parts such as annulus parts (a septum-side annulus part 205 and a lateral-wall-side annulus part 206) and a cardiac apex part 207, and extracting contour lines based on the set region of interest.

The search-range setting unit 9 sets an initial search range for carrying out template matching by setting an initial value of a search range in image data (step S103). If the initial search range is set large so as to reliably include the region of interest, the region of interest can be reliably set; however, the number of search pixels for setting the region of interest becomes excessive, and the calculation time for search becomes long. Therefore, the initial search range is preferred to reliably include the region of interest and be as small as possible. In the present embodiment, in order to set the initial search range that reliably includes the region of interest and is as small as possible, the reference coordinate (for example, the coordinate data of regions of interest or characteristic parts based on a plurality of pieces of past sample data) is read from the reference-coordinate storage unit of the region-of-interest database 12, and the initial search range is set based on the reference coordinate. The initial search range is only required to be set within the range of a predetermined number of pixels while using the reference coordinate (for example, the average of coordinate values of the sample data) as a center. The range of the predetermined number of pixels is only required to be a standard deviation of the coordinate values of the regions of interest or the characteristic parts based on the plurality of pieces of past sample data.

Figure 4:
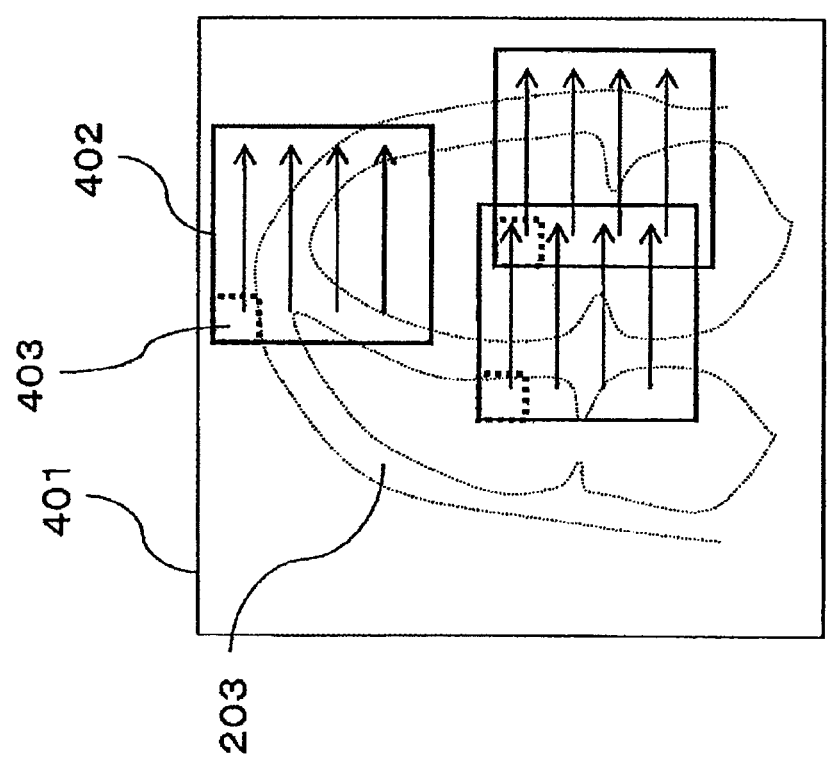
FIG. 4 is a drawing showing a comparative example of the first embodiment.

FIG. 4 is a drawing showing a comparative example of the present embodiment. In a search method shown in FIG. 4, a region of interest is set without reducing (compressing) image data. As shown in FIG. 4, a matching operation is carried out while moving a template 403 within a search range 402, and a position most well matched is set as a region of interest. Although the shape of the search range is not limited to a particular shape such as a circle or a rectangle, in the present embodiment a rectangle is taken as an example. In the comparative example, a massive number of matching operations have to be carried out, since the number of the pixels included in the search range is large. More specifically, the number of search pixels is excessive, and the calculation time of search is long. If the search range is large as in the comparative example, the region of interest can be reliably set in the search range; however, the calculation time for setting the region of interest becomes long, which is not preferred.

In the present embodiment, the image reducing unit (image-data compression unit) 10 carries out compression of image data based on a plurality of pixels to change the compression ratio of the image data, the search-range setting unit 9 sets a search range within the reduced (compressed) image data, and the region-of-interest setting unit 11 carries out setting of a region of interest including a characteristic part in the search range. More specifically, the image reducing unit (image-data compression unit) 10 compresses the image data by a first compression ratio (for example, data volume 1/4=compression ratio 1/4), the search-range setting unit 9 sets a first search range (for example, an initial search range) within the image data compressed by the first compression ratio, and the region-of-interest setting unit 11 sets a region of interest (including a characteristic part) within the first search range. Then, the image reducing unit (image-data compression unit) 10 compresses the image data by a second compression ratio (for example, data volume 1/2=compression ratio 1/2) by changing the compression ratio of the image data, the search-range setting unit 9 sets, within the image data compressed by the second compression ratio, a second search range including the region of interest set within the first search range, and the region-of-interest setting unit 11 sets a region of interest (including the characteristic part) within the second search range.

The image reducing unit (image-data compression unit) 10 carries out compression of the image data based on the plurality of pixels, to change the compression ratio of the image data. When the image reducing unit (image-data compression unit) 10 reduces (compresses) the image data, a method for simply thinning pixels (simple thinning method) may be used, or a method for smoothening brightness changes based on a neighborhood weighting average may be used. In the case of the former one, the calculation time is shortened. In the case of the latter one, the accuracy of template matching is improved.

Other than that, examples of the method for reducing (compressing) image data include a bicubic method (bicubic interpolation), a bilinear method (bilinear interpolation), and a nearest neighbor method (nearest neighbor interpolation).

Figure 5:
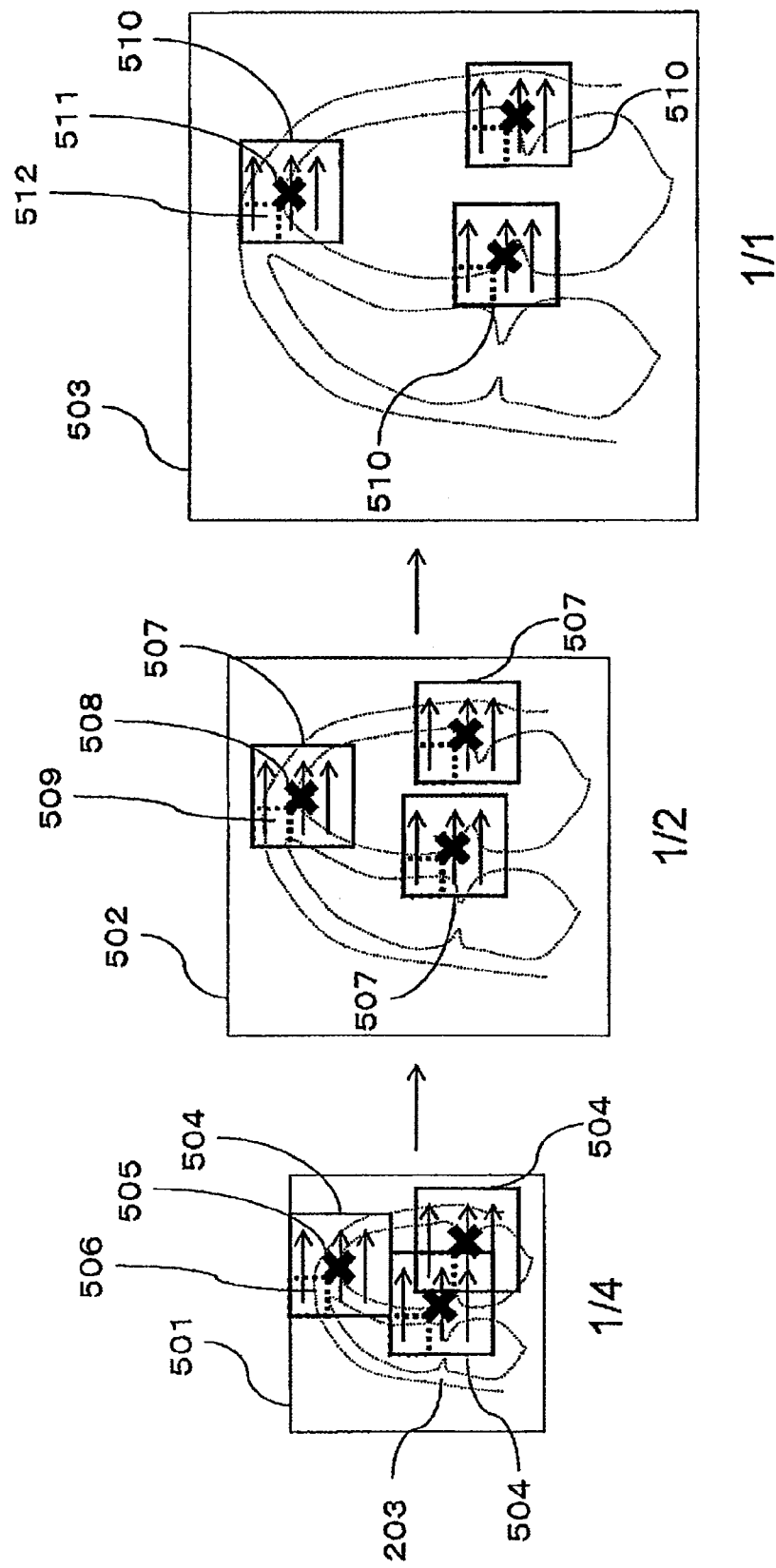
FIG. 5 shows drawings showing setting of search ranges in compressed image data by a search-range setting unit while changing the compression ratio (reduction ratio) of the image data.

As shown in FIG. 2, the image reducing unit (image-data compression unit) 10 compresses the image data and generates a reduced image (compressed image) (step S104). For example, as shown in FIG. 5, image data 501 is the image data obtained by compressing the image data of the medical image, which is obtained by the ultrasonic diagnostic device 1, into 1/4 (=compression ratio). More specifically, the image reducing unit (image-data compression unit) 10 compresses the image data of the ultrasonic image (medical image), which is generated by the ultrasonic-image generating unit 4, into 1/4 (each of vertical and horizontal side lengths by 1/2) to generate the image data 501. The initial search range created in step S103 is compressed into 1/4 and is set as a search range 504. More specifically, the search range (initial search range) 504 is set in the compressed image data so as to cover the range which is the same as that of the uncompressed image data obtained by the ultrasonic diagnostic device 1.

The coordinate of a center point 505 of the initial search range 504 is the reference coordinate stored in the region-of-interest database 12. The coordinate of the center point 505 is the coordinate of the region of interest or characteristic part (for example, the annulus part or cardiac apex part) based on the plurality of pieces of past sample data. More specifically, the center point 505 of the compressed image data is set at the same position (for example, the position of the same characteristic part) as that of the uncompressed image data, which has been obtained by the ultrasonic diagnostic device 1. In the present embodiment, the search range is determined according to the reference coordinate of the region of interest stored in the region-of-interest database 12. For example, there is set a search range that uses the average (reference coordinate) of the coordinate values of the regions of interest or characteristic part based on the plurality of pieces of past sample data as the center point 505 and uses the standard deviation of the coordinate values as the search range. Other than that, a search range that includes all or part (for example, 70% of the coordinate data) of the coordinate data of the regions of interest or the characteristic part based on the plurality of past sample data may be set.

Based on the template data stored in the region-of-interest database 12, a template 506 compressed into 1/4 is set. More specifically, the template 506 is set within the compressed image data so as to cover the same range as that in the uncompressed image data obtained by the ultrasonic diagnostic device 1.

Figure 6:
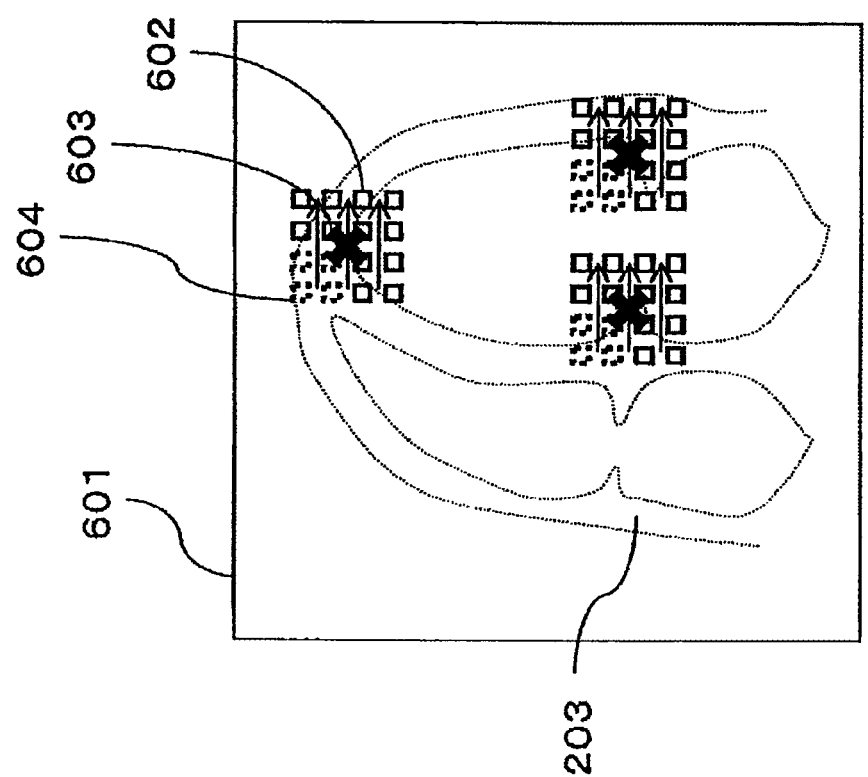
FIG. 6 is a drawing showing reducing (compressing) of image data and templates in search ranges by an image reducing unit (image-data compression unit).

When the image reducing unit (image-data compression unit) 10 reduces (compresses) the image data, as shown in FIG. 6, instead of reducing (compressing) all of the image data obtained by the ultrasonic diagnostic device 1, the image reducing unit (image-data compression unit) 10 reduces (compresses) the image data and the template within the search range. For example, the image data may be reduced (compressed) by thinning the pixels (pixels) of the search range and the template. In that case, in a case of 1/2 reduction of the image data, 1 pixel is reduced per 2 pixels; and, in a case of 1/4 reduction of the image data, 3 pixels are reduced per 4 pixels. FIG. 6 is a drawing showing an example of 1/4 reduction of image data. A search range 602 of FIG. 6 is a search range in which 3 pixels are removed (reduced) among 4 pixels (vertical 2 pixels×horizontal 2 pixels), and image data of 64 pixels (vertical 8 pixels× horizontal 8 pixels) is compressed into 16 pixels (vertical 4 pixels×horizontal 4 pixels). A template 604 of FIG. 6 is a template from which 3 pixels have been removed (reduced) among 4 pixels (vertical 2 pixels×vertical 2 pixels), wherein image data of 16 pixels (vertical 4 pixels×horizontal 4 pixels) is compressed into 4 pixels (vertical 2 pixels× horizontal 2 pixels). Practically, this is similar to image reduction by the above described simple thinning method; however, this method may be selected in consideration of readiness of implementation, etc.

With respect to the reduced (compressed) image data, the region-of-interest setting unit 11 of the ultrasonic diagnostic device 1 carries out setting of a region of interest including a characteristic part within the search range (step S105). For example, as shown in FIG. 5, the region-of-interest setting unit 11 moves the template 506 within the search range (initial search range) 504 of the image data 501 compressed into 1/4 and sets the most well matched position as the position of the region of interest. As a matching operation, a publicly known method such as the SAD method, subspace method, or Boosting is used, and learn data used therefor may be stored in the region-of-interest database 12 in advance.

Figure 7:
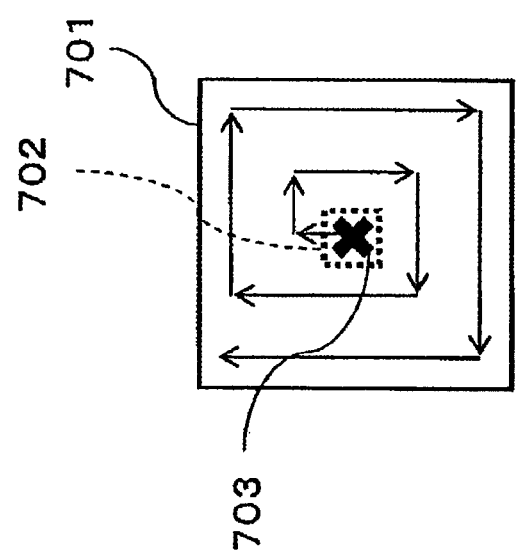
FIG. 7 is a drawing showing spiral movement of a template starting from a center point.

As shown in FIG. 5, the template 506 starts from the upper left of the search range 504 and moves from the left to the right and from the top to the bottom. However, as shown in FIG. 7, a template 702 may start from a center point 703 of a search range 701 and move spirally. Since the center point 703 is the coordinate (reference coordinate) of the region of interest or characteristic parts based on the plurality of pieces of past sample data, there is a high possibility that the position of the region of interest is set in the vicinity of the center point 703 of the search range 701. Therefore, the template 702 may be spirally moved to search the region of interest, the position having the correlativity of a predetermined threshold value or more with the template 702 may be set as the position of the region of interest, and the search may be terminated. As a result, the search time of the setting of the region of interest can be shortened.

The region-of-interest setting unit 8 of the ultrasonic diagnostic device 1 judges whether or not the setting of the region of interest or the characteristic part is to be terminated (step S106). When the region-of-interest setting unit 11 carries out setting of a region of interest including a characteristic part with respect to the image data which has been reduced (compressed) into 1/4, the setting resolution thereof also becomes 1/4. Therefore, the smaller the reduction ratio (compression ratio), the smaller the setting resolution, where the setting position of the region of interest or the characteristic part is set roughly. Whether or not the setting of the region of interest or the characteristic part is to be terminated may be judged according to at least one of the reduction ratio (compression ratio), the setting resolution, the setting processing time, and the number of setting processes.

If it is judged in step S106 to continue the setting of the region of interest or the characteristic part, the search-range setting unit 9 carries out setting of a search range so as to include the region of interest (characteristic part) set in step S105 (step S107). As described above, after the region of interest (including the characteristic part) is set in the first search range (for example, the initial search range) with respect to the image data compressed by the first compression ratio (for example, data volume 1/4=compression ratio 1/4), this search range is determined under the conditions that set a second search range including the coordinate of the region of interest, which has been set in the first search range, with respect to the image data compressed by a second compression ratio (for example, data volume 1/2=compression ratio 1/2). For example, as shown in FIG. 5, the coordinate of the region of interest (characteristic part) set in the initial search range (first search range) 504 of the image data 501 compressed by the compression ratio 1/4 (first compression ratio) is used as the coordinate of a center point 508 of a search range (second search range) 507 in image data 502 compressed by the compression ratio 1/2 (second compression ratio).

The search range 507 is set within a range of a predetermined number of pixels having the center point 508 as the center thereof. The predetermined number of pixels may be smaller than the standard deviation of the coordinate value of the region of interest or the characteristic part based on the plurality of pieces of past sample data. Other than that, there may be set a search range that includes part of the coordinate data (for example, 60% of the coordinate data) of the region of interest or the characteristic part based on the plurality of pieces of past sample data. In that case, the range that covers the search range (second search range) 507 may be smaller than the range covered by the search range (first search range) 504. The number of pieces of the coordinate data (for example, 60% of the coordinate data) covered by the search range (second search range) 507 may be smaller than the number of pieces of the coordinate data (for example, 70% of the coordinate data) covered by the search range (first search range) 504. This is for a reason that, since the set position of the region of interest or the characteristic part within the search range (first search range) 504 is set roughly, there is a high possibility that the position of the region of interest or the characteristic part is present in the vicinity of the center point 508, which is at the roughly set position.

Then, the process returns to step S104, and the image reducing unit (image-data compression unit) 10 carries out compression of the image data based on the plurality of pixels to change the compression ratio of the image data. In the present embodiment, as shown in FIG. 5, the image reducing unit (image-data compression unit) 10 compresses the image data of the ultrasonic image (medical image), which is generated by the ultrasonic-image generating unit 4, into 1/2 to generate the image data 502. Thus, the second compression ratio (compression ratio 1/2) is larger than the first compression ratio (compression ratio 1/4).

The region-of-interest setting unit 11 sets a region of interest in the second search range. For example, as shown in FIG. 5, the region-of-interest setting unit 11 moves a template 509 within the search range (second search range) 507 of the image data 502, which has been compressed into 1/2, and sets the most well matched position as the position of the region of interest (step S105).

The region-of-interest setting unit 8 of the ultrasonic diagnostic device 1 judges whether or not to terminate the setting of the region of interest or the characteristic part (step S106). In the present embodiment, until the image data (data volume 1/1=compression ratio 1/1) of the ultrasonic image (medical image) generated by the ultrasonic-image generating unit 4 is obtained, the reduction ratio (compression ratio) is changed to set the region of interest or the characteristic part. However, if the accuracy of the position at a level that sufficiently satisfies demands is obtained with a data volume 1/4 (compression ratio 1/4) or a data volume 1/2 (compression ratio 1/2), the process of setting the region of interest or the characteristic part may be terminated at an intermediate reduction ratio (compression ratio). If the setting is carried out up to the image data at the compression ratio of 1/1, steps S107, S104, and S105 are further carried out to change the reduction ratio (compression ratio) and set the position of the region of interest (characteristic part).

For example, as shown in FIG. 5, the coordinate of the region of interest (characteristic part) set within the search range (first search range) 507 of the image data 502 compressed by the compression ratio 1/2 (first compression ratio) is used as the coordinate of a center point 511 of a search range (second search range) 510 in image data 503 compressed by a compression ratio 1/1 (second compression ratio), and the region-of-interest setting unit 11 moves a template 512 within the search range (second search range) 511 of the image data 503, which is at the compression ratio 1/1, and sets the most well matched position as the position of the region of interest (step S105).

The finally set positions are the positions of the regions of interest including the characteristic parts (the annulus parts 205 and 206 and the cardiac apex part 207) of FIG. 3. In the present embodiment, an example in which the reduction ratio (compression ratio) of the image data is in three levels of 1/4, 1/2, and 1/1 has been explained. However, arbitrary reduction ratios (compression ratios) can be set.

Figure 8:
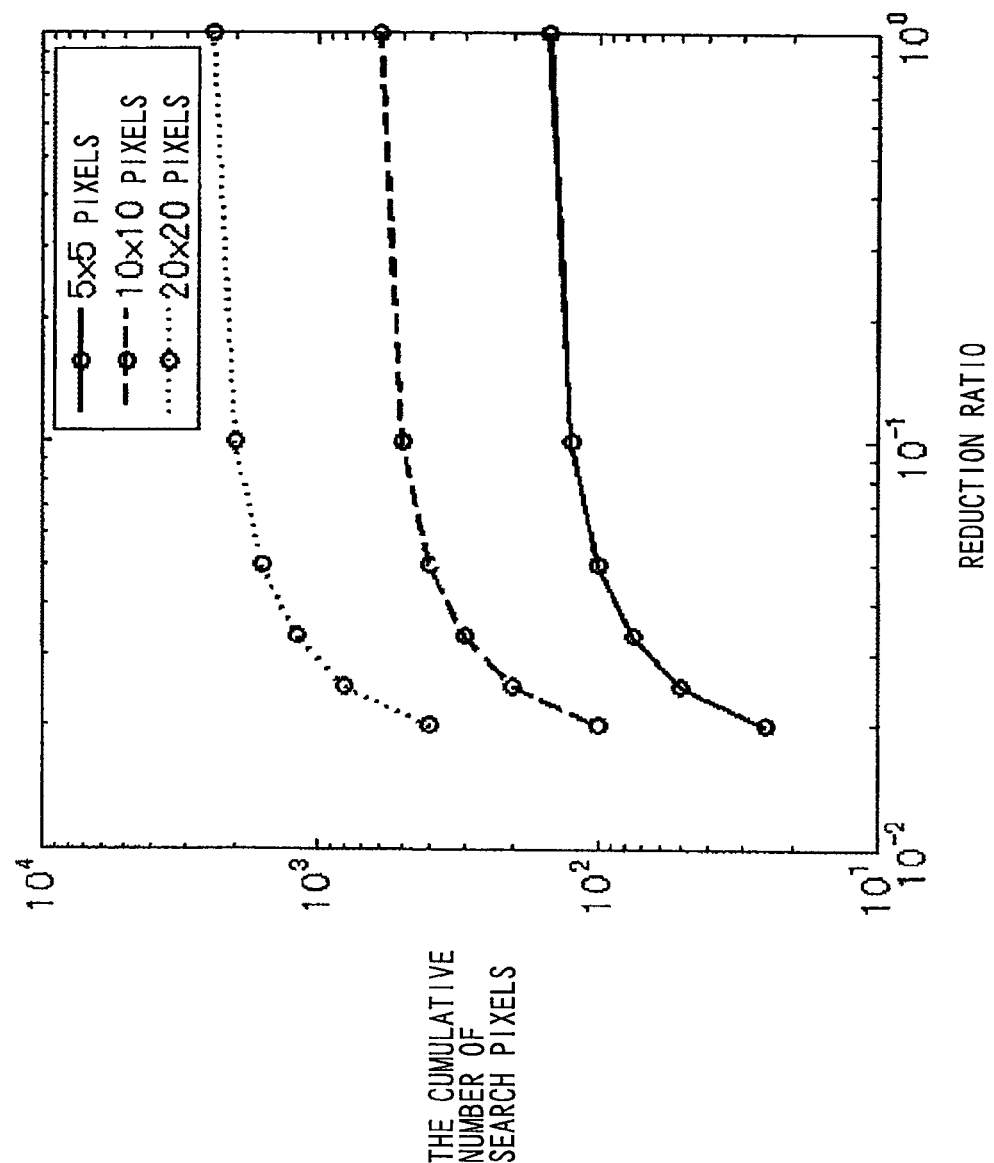
FIG. 8 is a drawing showing the relation between the reduction ratios of the image data of the first embodiment of the present invention and the cumulative number of search pixels.

Next, the relation between the reduction ratio (compression ratio) and the number of search pixels will be explained. FIG. 8 shows the relation between the reduction ratios of the image data (for example, consisting of 128×128 pixels, 256×256 pixels) of the present embodiment and the cumulative numbers of search pixels. The reduction ratios of FIG. 8 are in six levels of 1/50, 1/40, 1/30, 1/20, 1/10, and 1/1. The number of the search pixels is the number of the pixels within the search range. In a case of a search range of 5 vertical pixels×5 horizontal pixels, the number is 25 pixels.

Herein, explanations will be given on the assumption that the number of the search pixels is 5×5 pixels=25 pixels at any reduction ratio. As shown in FIG. 8, if the number of the search pixels is 25 pixels, the cumulative number of the search pixels becomes 25 (reduction ratio 1/50), 50 (reduction ratio 1/40), 75 (reduction ratio 1/30), 100 (reduction ratio 1/20), 125 (reduction ratio 1/10), and 150 (reduction ratio 1/1) from the reduction ratios 1/50 toward 1/1. Therefore, if the setting of the region of interest or the characteristic part is carried out from the image data of the reduction ratios 1/50 to 1/1, the number of the matching operations becomes 150 in total.

On the other hand, in the comparative example as shown in FIG. 4, if a region of interest is set (at a reduction ratio 1/1) within a search range, which is the same range as a search range of 5×5 pixels at a reduction ratios 1/50, without reducing (compressing) the image data, the number of pixels within the search range becomes (5 pixels×50)×(5 pixels× 50)=62500, and 62500 matching operations are required as the number of times thereof. Therefore, according to the present embodiment, the search time of the setting of the region of interest can be shortened by recursively setting regions of interest on a plurality of pieces of image data having different reduction ratios (compression ratios).

In the example of FIG. 8, the reduction ratios are in six levels, but may be in an arbitrary number of levels (for example, four levels of 1/40, 1/30, 1/20, and 1/10); more specifically, search ranges of a plurality of pieces of image data generated after the compression can be arbitrarily selected, and a region of interest can be set in the medical image based on the selected search range. The number of the matching operations in this case becomes 50 (reduction ratio 1/40), 75 (reduction ratio 1/30), 100 (reduction ratio 1/20), and 125 (reduction ratio 1/10). Therefore, if the setting of regions of interest or characteristic parts is carried out from the image data of the reduction ratios 1/40 to 1/10, the number of the matching operations becomes 125 in total. In this manner, the number of the levels of the reduction ratios can be changed in accordance with the required setting precision or allowable calculation time. In other words, there are formed a plurality of levels in which the search ranges of the plurality of pieces of image data generated after the compression are arranged in accordance with compression ratios, a level can be arbitrarily selected from the formed levels, and a region of interest can be set within the medical image based on the search range of the selected level. The number of the levels of the reduction ratios (compression ratios) is used when the region-of-interest setting unit 8 judges whether to terminate the setting of the region of interest or the characteristic part in step S106 of FIG. 2.

Moreover, as shown in FIG. 8, in a case in which the number of the search pixels is 10×10 pixels=100 pixels, if setting of the region of interest or the characteristic part is carried out up to the image data of the reduction ratio 1/1, the number of the matching operations becomes 600. Moreover, in a case in which the number of the search pixels is 20×20 pixels=400 pixels, the number of the matching operations becomes 2400. In this manner, in accordance with demands for search time reduction, accuracy, etc., the search range and the reduction ratio (compression ratio) can be arbitrarily selected.

In step S106, if it is judged that the region of interest or the characteristic part has been set and the setting is to be terminated, the set region of interest is set as a desired region of interest (step S108). Thus, the region of interest is set for measurement by the measurement unit 13. If the desired region of interest or characteristic part is a point, the point set in step S105 becomes the position of the region of interest. If the region of interest is a line or a region, a predetermined region-of-interest generating process is carried out. For example, in a case in which the measurement unit 13 is to measure the volume of the heart, a region-of-interest generating process of extracting the contour of the heart is carried out. As shown in FIG. 3, if the annulus parts 205 and 206 and the cardiac apex part 207 are set as a region of interest (characteristic part), the contour line (curved line) 208 which passes through the annulus parts 205 and 206 and the cardiac apex part 207 is generated. Examples of the method for generating the curved line 208 include a polynomial-expression curved line and a dynamic contour model.

The measurement unit 13 carries out a measurement operation about the measurement item set by the input unit 7 (step S109). In the present embodiment, the measurement unit 13 calculates the volume value of the left ventricle by utilizing the above-described contour of the heart by applying a Modified Simpson method.

The output/display unit 6 displays the result of the measurement (step S110). For example, as shown in FIG. 3, the volume value of the left ventricle calculated by the measurement unit 13 is displayed in the measurement-value field 204. The annulus parts 205 and 206, the cardiac apex part 207, and the contour line 208 set may be displayed on the ultrasonic image in a superimposed manner.

Hereinabove, the first embodiment according to the present invention has been explained. However, the present invention is not limited thereto, and changes/modifications can be made within the range described in claims.

For example, the search ranges are set in steps S103 and S107 of FIG. 2. In this case, the region-of-interest database 12 including the reference-coordinate storage unit may store a reference coordinate which serves as a reference of the position of the region of interest, and the search ranges may be set based on a coordinate difference between the coordinate of the set region of interest and the reference coordinate. The search ranges may be set so that the coordinate difference is minimized.

There is a high possibility that the position of the region of interest or the characteristic part is present in the vicinity of the position of the region of interest (reference coordinate) of the plurality of pieces of past sample data. Therefore, the search range is preferably determined so as to minimize the coordinate difference between the reference coordinate based on the plurality of pieces of past sample data and the set region of interest.

Figure 9:
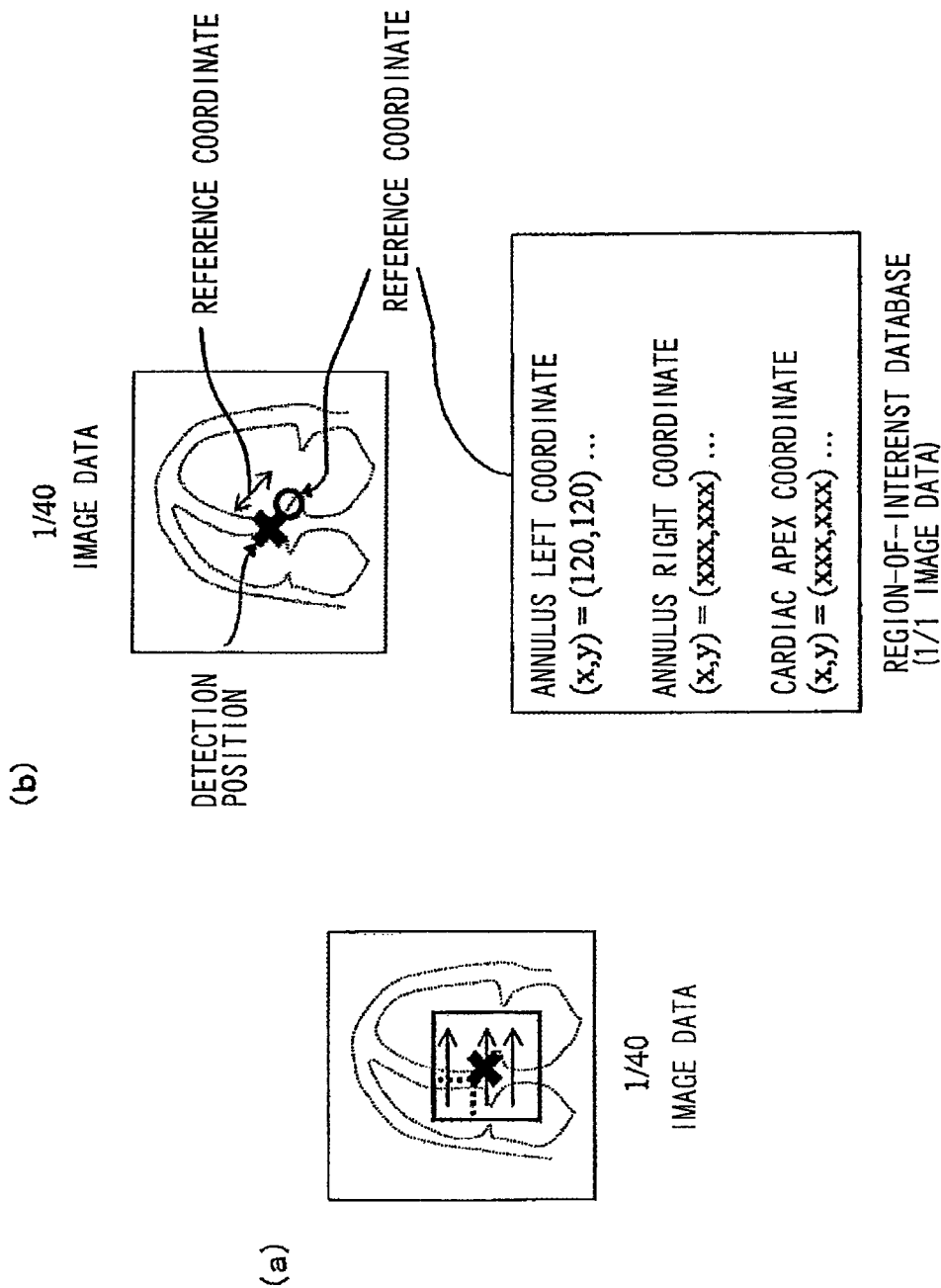
FIG. 9 shows drawings showing that a coordinate difference is calculated based on a plurality of search ranges, and a search range is set so as to minimize the coordinate difference.

FIG. 9 shows drawings showing an example of determining a search range within image data of a reduction ratio 1/40. As shown in FIG. 9, the search-range setting unit 9 sets the search range within the image data of the reduction ratio 1/40. For example, the search-range setting unit 9 expands the coordinate value of the search range, which is set in the image data of a smaller reduction ratio which is a reduction ratio 1/48, by 48/40-fold and sets the search range which is the same range as that of the reduction ratio 1/48 within the image data of the reduction ratio 1/40. The reference coordinate (for example, the average of the coordinate values of the sample data) stored in the region-of-interest database 12 is read. If (x, y)=(120, 120) when the reduction ratio is 1/1, the position of the reference coordinate corresponds to (x, y)=(3, 3) in a case of image data of a reduction ratio 1/40. The region-of-interest setting unit 11 sets the coordinate difference (error) between the set position of the region of interest (characteristic part) and the reference coordinate. For example, if the set position of the region of interest is (x, y)=(4, 4) and the position of the reference coordinate is (x, y)=(3, 3), the coordinate difference is calculated as a Euclidean distance.

By using the plurality of pieces of sample data, for each piece of sample data, the region-of-interest setting unit 11 may calculate the coordinate difference between the position (reference coordinate) of the region of interest of the sample data and the position of the set region of interest. In that case, the average of a plurality of coordinate differences is calculated. Based on a plurality of search ranges, the coordinate differences are calculated, and a search range is set so that the coordinate difference is minimized. Also at other reduction ratios, search ranges are similarly set.

Figure 10:
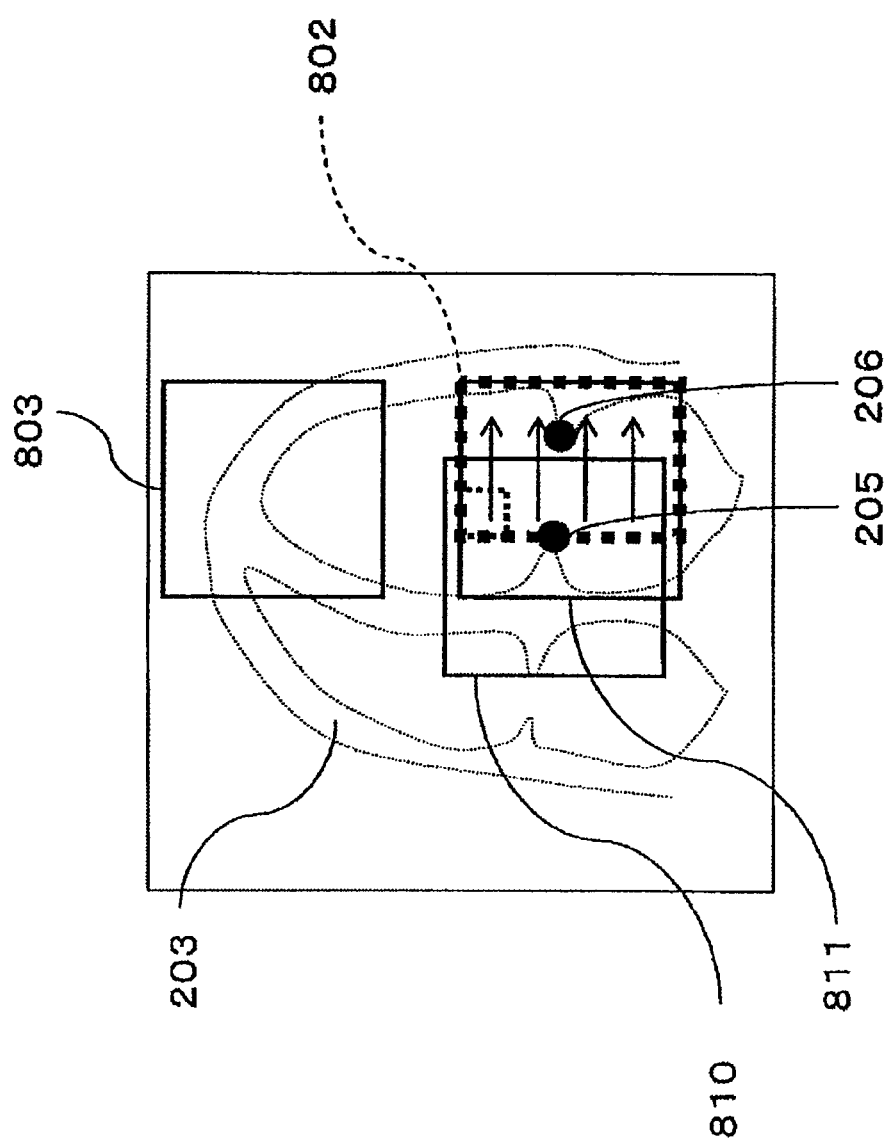
FIG. 10 is a drawing showing that, when one of annulus parts is set, within a limitation of a search range to the left side or the right side of the position of the annulus part, the other annulus part is set.

When a first region of interest is set within a range overlapped with the above-described plurality of search ranges in step S105 of FIG. 2, based on the position of the set first region of interest, the region-of-interest setting unit 11 sets a second region of interest within a limitation in part of the search ranges. For example, as shown in FIG. 10, a search range 810 includes the septum-side annulus part (the first region of interest or the first annulus part) 205 of the heart, a search range 811 includes the lateral-wall-side annulus part (the second region of interest or the second annulus part) 206 of the heart, and the septum-side annulus part (first annulus part) 205 is positioned to the left side of the lateral-wall-side annulus part (the second annulus part) 206; in this case, the region-of-interest setting unit 11 sets the lateral-wall-side annulus part (the second annulus part) 206 within a limitation in a search range 802 to the right side of the septum-side annulus part (the first annulus part) 205.

Normally, the lateral-wall-side annulus part 206 is set to the right side of the septum-side annulus part 205. Therefore, when the lateral-wall-side annulus part 206 is to be searched for, setting of the lateral-wall-side annulus part 206 is preferably carried out within the search range 802 to the right side of the septum-side annulus part 205.

On the other hand, when the lateral-wall-side annulus part (the first annulus part) 206 is positioned to the right side of the septum-side annulus part (the second annulus part) 205, the region-of-interest setting unit 11 sets the septum-side annulus part (the second annulus part) within a limitation in a search range to the left side of the lateral-wall-side annulus part (the first annulus part) 206.

Figure 11:
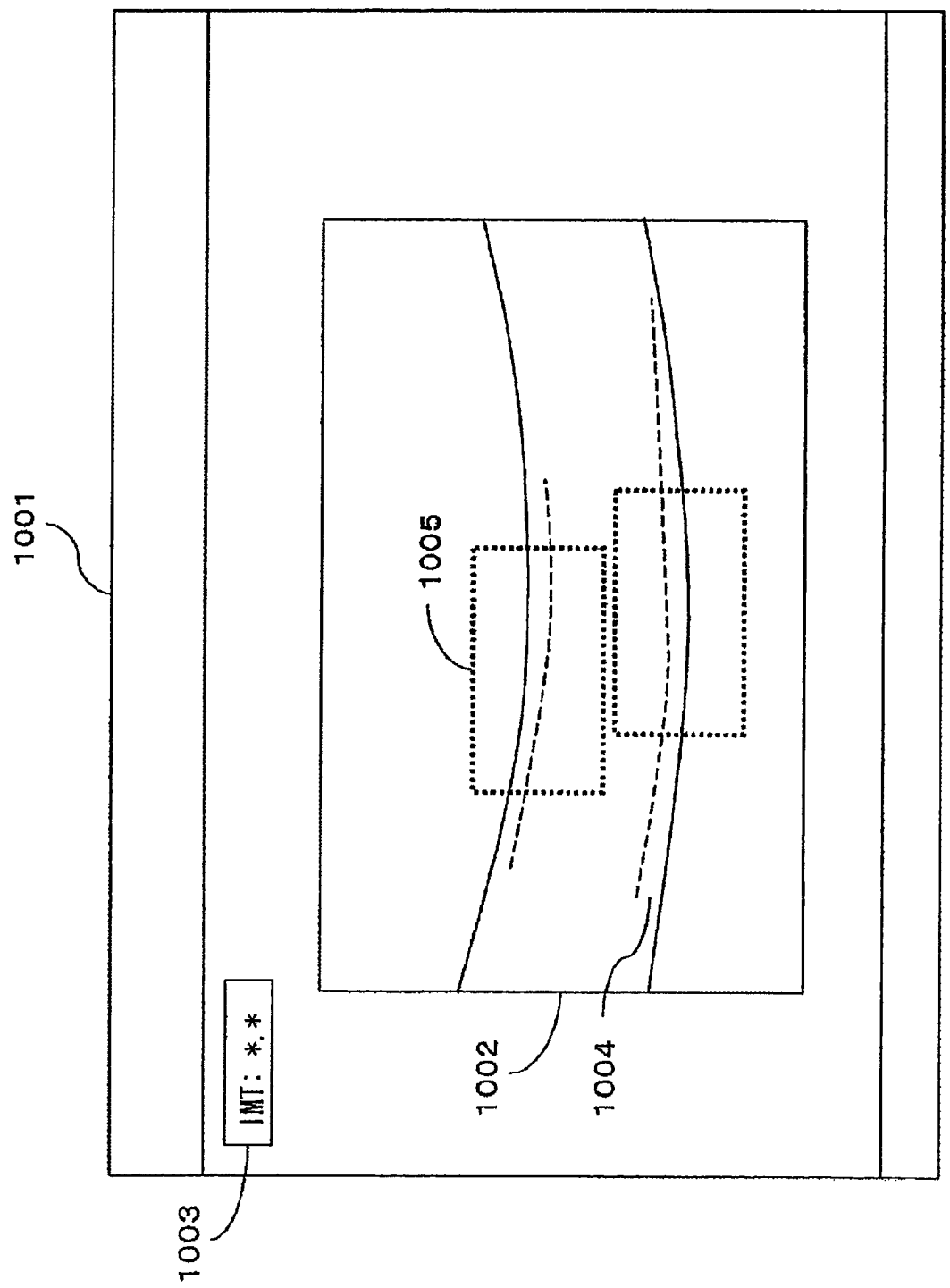
FIG. 11 is a drawing showing that a region of interest is set on B-mode image data when an IMT measurement application is used.

As an example of applying the present embodiment to another application, setting of a region of interest by a measurement application of IMT will be shown. As shown in FIG. 11, also in a case in which the IMT measurement application is used, the region of interest is set on B-mode image data. Therefore, the region-of-interest database 12 stores the coordinate (reference coordinate) of regions of interest set in past IMT measurement (sample data) and a template of an IMT measurement image, and setting of a region of interest is carried out in a manner similar to the flow chart of FIG. 2.

As a result, in IMT measurement, when the selected measurement item is input by an examiner, there can be realized an application of setting a region of interest at an IMT measurement position and calculating and displaying a measurement value. FIG. 11 is a drawing showing an example in which a region of interest 1005 for measuring the thickness of an intima-media complex 1004 is set on carotid-artery image data 1002.

According to the present embodiment, when the examiner sets a measurement item, the region of interest matching the measurement item can be set. By setting the initial search range based on the reference coordinate stored in the region-of-interest database 12 and carrying out search (retrieval) of the region of search while changing the reduction ratio (compression ratio), the region of interest can be set within the search range in which the possibility of presence of the region of interest is high. Moreover, by recursively setting the region of interest by using the plurality of pieces of image data of different reduction ratios, as compared with the case where the image data is not reduced (image data of a reduction ratio 1/1), the search range can be narrowed in each of the pieces of reduced image data, and the number of times of matching can be reduced, and therefore high-speed setting processing can be carried out. Therefore, accuracy improvement of the setting of the region of interest and search time reduction can be achieved by setting the search range by using the compressed image data and setting the region of interest by, for example, template matching. Thus, there can be provided a medical image diagnostic device which reduces the operation load of region-of-interest setting of the examiner.

In the present invention, a medical image of a subject is captured by the image capturing unit 20, the image-data compression unit 10 uses image data of the captured medical image of the subject as uncompressed image data and generates compressed image data by compression based on a plurality of pixels of the uncompressed image data, the search-range setting unit 9 sets a search range of the compressed image data and sets a search range of the uncompressed image data, and the region-of-interest setting unit 8 sets a region of interest within the medical image based on the search range of the uncompressed image data and the search range of the compressed image data.

Specifically, the medical image diagnostic device of the present invention is provided with: an image capturing unit 20 that captures a medical image of a subject; an image-data compression unit 10 that uses image data of the captured medical image of the subject as uncompressed image data and generates compressed image data by compression based on a plurality of pixels of the uncompressed image data; a search-range setting unit 9 that sets a search range of the compressed image data and sets a search range of the uncompressed image data; and a region-of-interest setting unit 8 that sets a region of interest within the medical image based on the search range of the uncompressed image data and the search range of the compressed image data.

According to this configuration, by setting the search range by using the compressed image data and setting the region of interest, for example, by template matching, search time reduction for setting the region of interest can be achieved in a case where the region of interest is set in real time. Moreover, according to this configuration, by setting the region of interest in the image data of a small compression ratio and gradually increasing the compression ratio, accuracy of setting of the region of interest can be improved.

In the medical image diagnostic device of the present invention, the search-range setting unit 9 sets the second search range in a size equal to the first search range.

According to this configuration, since the second search range and the first search range are equal in size, in a case where processing of the search ranges is distributed to and carried out by a plurality of processors, if processing start of the plurality of processors is simultaneous, termination time thereof is the same. Therefore, a waiting process until the processing termination among the plurality of processors is not required to be carried out. Therefore, corresponding to the period that does not require the waiting process, the search time for setting the region of interest can be shortened in a case where the region of interest is set in real time.

The medical image diagnostic device of the present invention is provided with a reference-coordinate storage unit 12 that stores a reference coordinate serving as a reference of the position of the region of interest, wherein the search-range setting unit 9 sets the search range based on the reference coordinate.

According to this configuration, the position of the initial search range can be set by using the reference coordinate, and the search range can be set so as to include the reference coordinate.

In the medical image diagnostic device of the present invention, the search-range setting unit 9 uses the reference coordinate, which is an average of a coordinate value of a region of interest based on sample data, as a center and sets a standard deviation of the coordinate value of the region of interest as the search range.

According to this configuration, the position of the search range can be set by using the reference coordinate as the center, and the search range can be set by using the standard deviation of the coordinate value of the region of interest based on the sample data.

In the medical image diagnostic device of the present invention, the search-range setting unit 9 sets a reference coordinate, which is a coordinate value of a characteristic part set in a contour extracting process, as a center of the search range.

According to this configuration, the characteristic part is set in the contour extracting process. Therefore, even if the contour extracting process is not highly precise, the search range can be narrowly adjusted while maintaining the positional relation of the characteristic part, and accuracy in setting of the region of interest is also improved.

The medical image diagnostic device of the present invention is provided with a reference-coordinate storage unit 12 that stores a reference coordinate serving as a reference of the position of the region of interest, wherein the search-range setting unit sets the search range based on a coordinate difference between a coordinate of the set region of interest and the reference coordinate.

According to this configuration, there is a high possibility that the position of the region of interest is present in the vicinity of the reference coordinate. Therefore, accuracy in setting of the region of interest is improved by setting the search range based on the coordinate difference between the coordinate of the set region of interest and the reference coordinate.

In the medical image diagnostic device of the present invention, the search-range setting unit 9 sets the search range so that the coordinate difference is minimized.

According to the configuration, the accuracy in setting of the region of interest is improved by setting the search range so that the coordinate difference between the reference coordinate and the set region of interest is minimized.

In the medical image diagnostic device of the present invention, when a first region of interest is set in a range overlapped with a plurality of the search ranges, based on the position of the first region of interest, the region-of-interest setting unit 8 sets a second region of interest within a limitation in part of the search range.

According to this configuration, if the search ranges are overlapped, the setting time of the region of interest can be shortened by setting the region of interest within a limitation in part of the search ranges.

In the medical image diagnostic device of the present invention, the region-of-interest setting unit 8 sets a region including a first annulus part of the heart as the first region of interest; sets a region including a second annulus part of the heart as the second region of interest; if the first annulus part is positioned to the left side of the second annulus part, sets the second annulus part within a limitation in the search range to the right side of the first annulus part; and, if the first annulus part is positioned to the right side of the second annulus part, sets the second annulus part within a limitation in the search range to the left side of the first annulus part.

According to this configuration, since the annulus parts are present to the left and the right, respectively, if one of the annulus parts is set, within the limitation of the search range to the left side or the right side of the position of the annulus part, the other annulus part may be set. As a result, the search range can be narrowed, and the set time of the region of interest can be shortened.

The medical image diagnostic device of the present invention is provided with a measurement unit 13 that measures a measurement item in the set region of interest; wherein the measurement unit outputs a measurement result of the measurement item after the region of interest is set within at least one of the first search range and the second search range.

According to this configuration, the measurement result of the measurement item may be output after the region of interest is set in the second search range, and the measurement results of the measurement item may be output after the region of interests are set in the first search range and the second search range. In accordance with the output results, setting of the region of interest can be stopped at desired timing.

In the medical image diagnostic device of the present invention, the region-of-interest setting unit 8 terminates setting of the region of interest based on an appropriate value of the measurement result.

According to this configuration, in accordance with the appropriate value of the output result, setting of the region of interest can be stopped at desired timing.

A region-of-interest setting method of a medical image diagnostic device of the present invention includes: capturing a medical image of a subject by an image capturing unit 20; using image data of the captured medical image of the subject as uncompressed image data and generating compressed image data by compression based on a plurality of pixels of the uncompressed image data by an image-data compression unit 10; setting a search range of the compressed image data and setting a search range of the uncompressed image data by the search-range setting unit 9; and setting a region of interest in the medical image based on the search range of the uncompressed image data and the search range of the compressed image data by a region-of-interest setting unit 8.

Second Embodiment

Hereinafter, a medical image diagnostic device according to a second embodiment will be explained by reference to drawings. Unless otherwise stated, other configurations are similar to those of the medical image diagnostic device according to the first embodiment.

The present embodiment shows an example of an application of setting a region of interest on image data of a B mode and a measurement value and performing the measurement. In the present embodiment, in order to obtain image data of Doppler or an M mode, a region of interest is set on the image data of the B mode. Moreover, in the present embodiment, a region of interest including a predetermined measurement position is set in the image data of the measurement value about the measurement item of Doppler or the M mode. Furthermore, by combining the image data about the B mode and the measurement value, a plurality of regions of interest may be set.

The image reducing unit (image-data compression unit) 10 carries out compression of image data based on a plurality of pixels to change the compression ratio (reduction ratio) of the image data. The search-range setting unit 9 sets a search range within the compressed image data. The region-of-interest setting unit 11 carries out setting of a region of interest, which includes a characteristic part, within the search range. Then, the image reducing unit (image-data compression unit) 10 compresses image data (image data of the B mode or measurement value) by a first compression ratio, the search-range setting unit 9 sets a first search range in the image data compressed by the first compression ratio, and the region-of-interest setting unit 11 sets a region of interest within the first search range. Furthermore, the image reducing unit (image-data compression unit) 10 compresses the image data (the image data of the B mode or measurement value) by a second compression ratio, the search-range setting unit 9 sets a second search range, which includes the region of interest set in the first search range, within the image data compressed by the second compression ratio, and the region-of-interest setting unit 11 sets a region of interest within the second search range.

Figure 12:
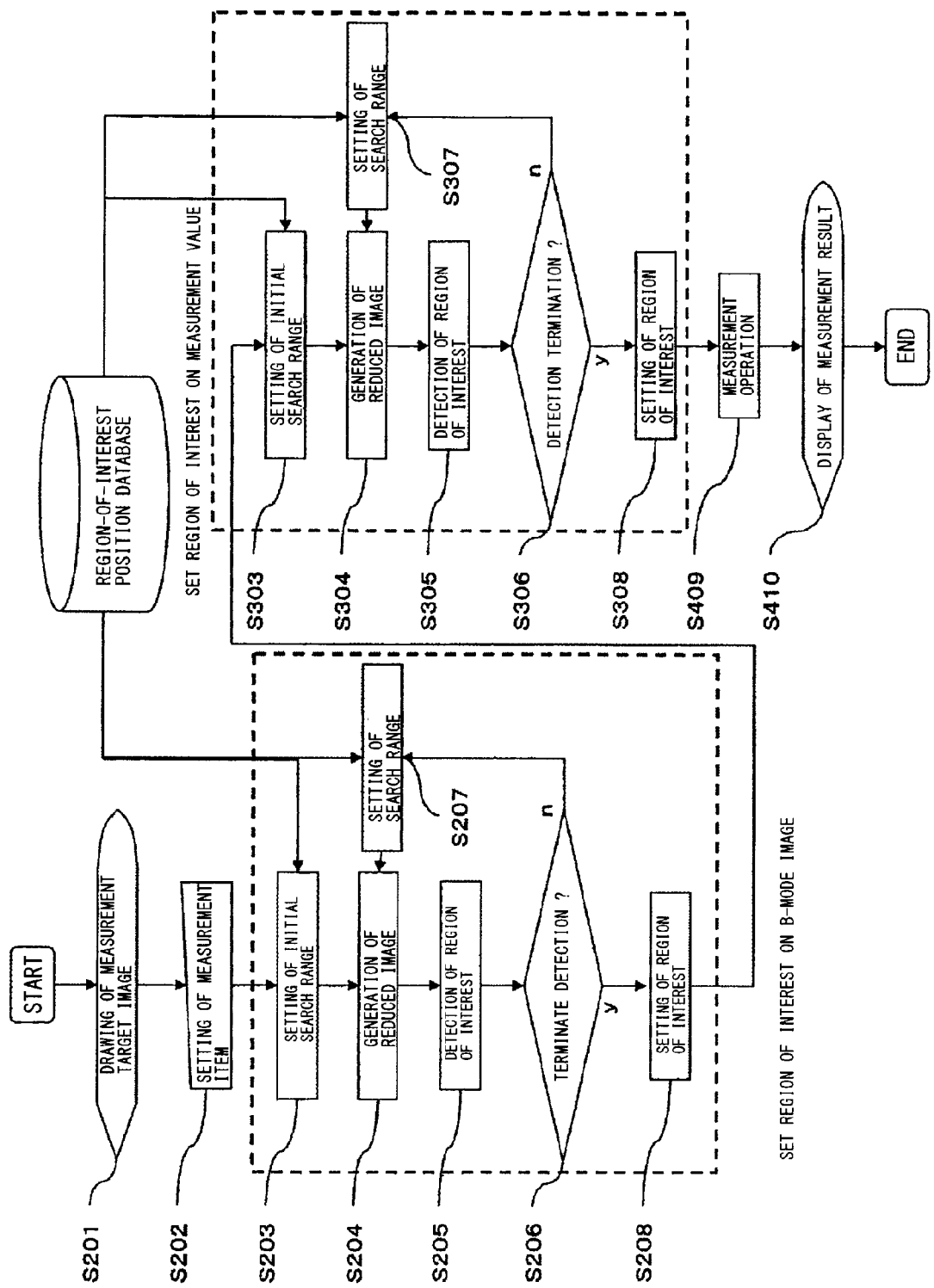
FIG. 12 is a flow chart explaining operation of a medical image diagnostic device according to a second embodiment of the present invention.
Figure 13:
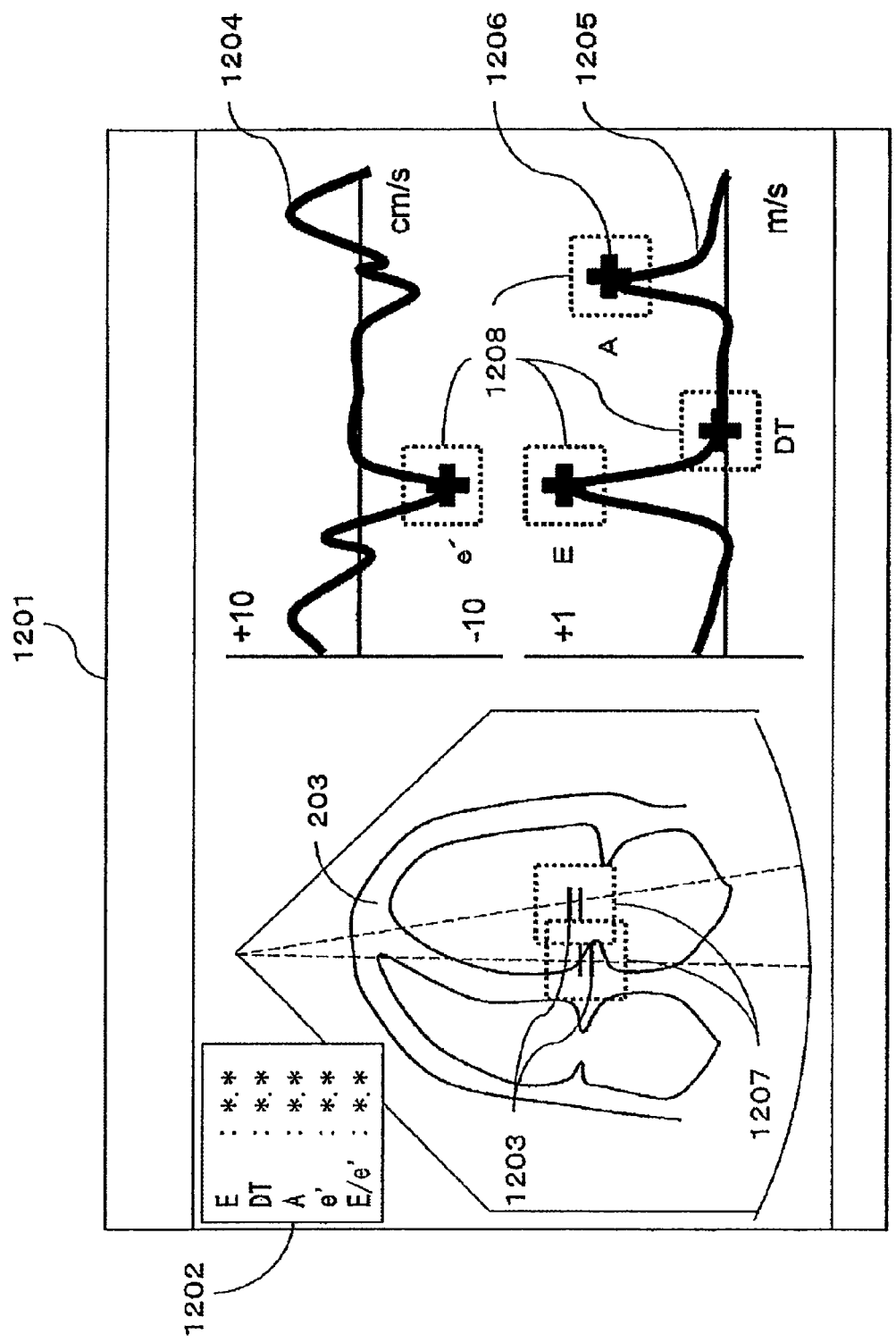
FIG. 13 is a drawing showing an example of bidirectional Doppler measurement.
Figure 14:
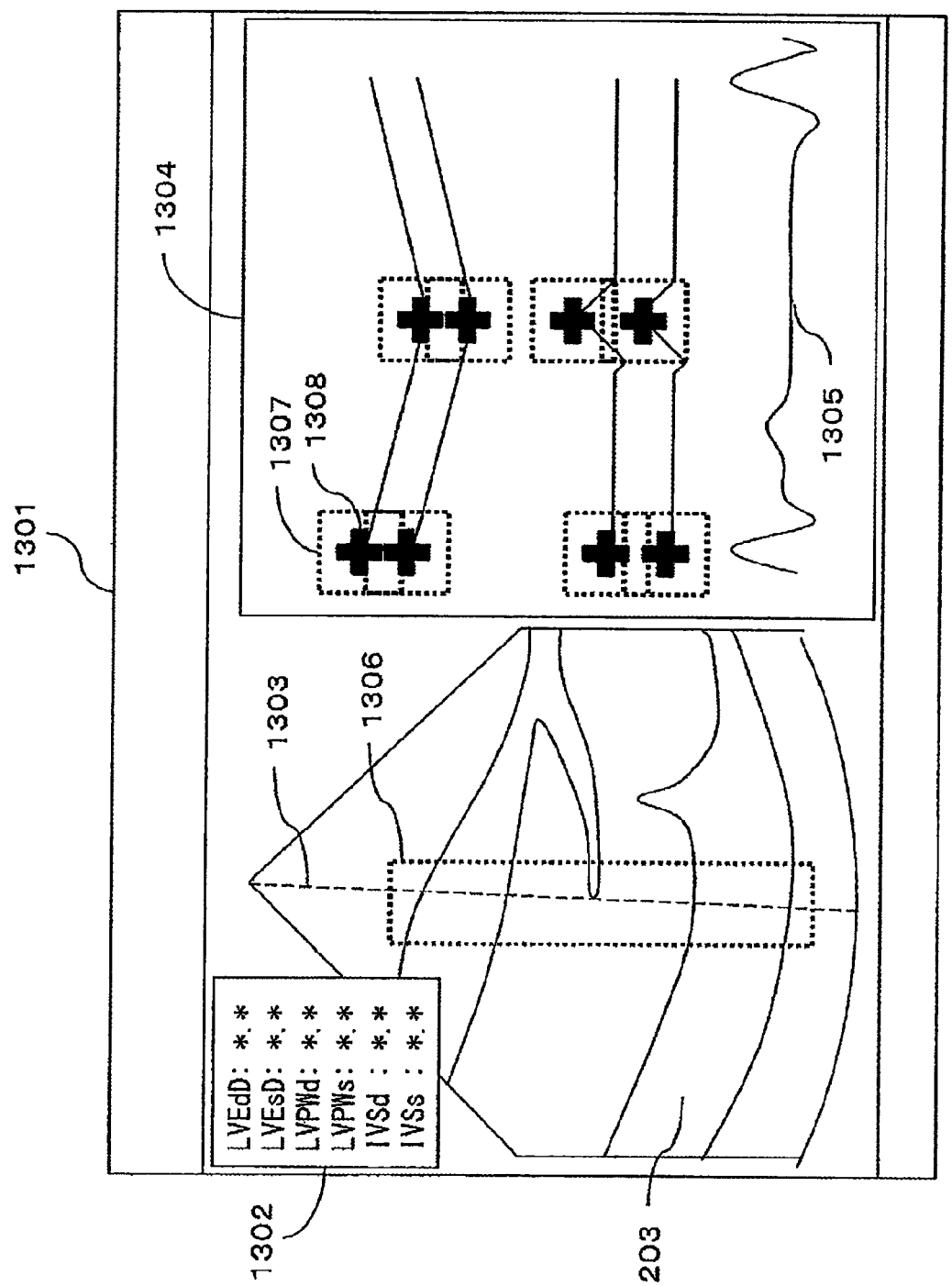
FIG. 14 is a drawing showing an example of left ventricle measurement in image data of an M mode.

FIG. 12 is a flow chart explaining operations of the medical image diagnostic device according to the present embodiment. FIG. 13 is a drawing showing an example of bidirectional Doppler measurement. FIG. 14 is a drawing showing an example of measurement of the left ventricle in the image data of the M mode.

As shown in FIG. 12, an image on which a living-body tissue serving as a target is drawn on the display screen of the output/display unit 6 is displayed (step S201). As the living-body tissue serving as the target, FIG. 13 shows image data of a cardiac-apex 4-chamber, and FIG. 14 shows image data of parasternal long-axis view.

A measurement item is set by an examiner by using the input unit 7 (step S202). For example, if an inflow blood-flow velocity or an annulus-part moving velocity serves as the measurement item in bi-directional Doppler of FIG. 13, Doppler gates 1203 have to be set at a valve orifice and the annulus part. As shown in FIG. 14, if the size of a left ventricle wall or cavity is the measurement item in the M mode, an M-mode beam line 1303 has to be set on the B-mode image data.

The region-of-interest setting unit 8 sets a region of interest including characteristic parts (annulus, valve orifice, etc.) at which the Doppler gates 1203 or the M-mode beam line 1303 are set, to thereby set the region of interest. The output/display unit 6 displays a Doppler image or an M-mode image. These operations are carried out through step S203 to step S207 and are similar to step S103 to step S107 shown in FIG. 7. However, the region-of-interest database 12 including the reference-coordinate storage unit stores the positions (reference coordinates) of the annulus, valve orifice, and M-mode beam line obtained as a plurality of pieces of past sample data and templates. The reference coordinate (for example, the coordinate data of the region of interest or the characteristic part based on a plurality of pieces of past sample data) is read from the reference-coordinate storage unit of the region-of-interest database 12, and a search range is set based on the reference coordinate.

Then, a region of interest is set while changing the reduction ratio (compression ratio) of the image data to thereby set the region of interest on the B-mode image data (step S208).

Moreover, in the present embodiment, a region of interest including the measurement position of the measurement item is set within the image data about the measurement item of Doppler or the M mode (step S303 to step S308).

In the upper right of FIG. 13, image data of TDI (measurement value) within a region of interest 1207 set in the B-mode image is shown; and, in the lower right of FIG. 13, image data of pulse Doppler (measurement value) is shown.

In the right of FIG. 14, the image data of the M mode in the M-mode beam line 1303 of a region of interest 1306 set in the B-mode image is shown.

The region-of-interest setting unit 8 sets a region of interest, which includes a predetermined measurement position, within the image data of the measurement value about the measurement item of Doppler or the M mode. More specifically, the region-of-interest setting unit 8 sets regions of interest (measurement positions) within the image data. In FIG. 13, waveform positions 1206 are set as the regions of interest (measurement positions) of E waves, A waves, e' waves, and DT (E-wave slow-down time). In FIG. 14, wall positions 1308 are set as regions of interest (measurement positions) of the endocardium/epicardium of the cardiac muscle. These operations are carried out through step S303 to step S307, which are similar to step S103 to step S107 or step S203 to step S207.

However, the region-of-interest database 12 stores the positions (reference coordinates) of the E waves, A waves, e' waves, and DT in Doppler images and a template 1208 and stores the positions (reference coordinates) of the endocardium/epicardium in M-mode images and a template 1307. The reference coordinate (for example, the coordinate data of the region of interest or characteristic part based on the plurality of pieces of past sample data) is read from the reference-coordinate storage unit of the region-of-interest database 12, and a search range is set based on the reference coordinate.

Then, the region of interest is set while changing the reduction ratio (compression ratio) of the image data, and the region of interest (measurement position) is set on the image data about the measurement item of Doppler or the M mode (step S308). In the present embodiment, since the region of interest (measurement position) is a point, the region of interest set by the region-of-interest setting unit 11 serves as the measurement position for measurement without change. If the region of interest is a line or a region, a predetermined region-of-interest generating process is carried out.

Then, the measurement unit 13 carries out a measurement operation in the set region of interest (S409). In the Doppler measurement of FIG. 13, the measurement unit 13 calculates the values of the E waves, A waves, e' waves, and DT from Doppler waveforms at the waveform positions (measurement positions) 1206. Also, the measurement unit 13 may calculate E/e' which is a combination of the measurement values. In the M-mode measurement of FIG. 14, the measurement unit 13 calculates measurement values about the size of the cardiac muscle and the cardiac cavity such as LVEdD (left ventricular end-diastolic diameter) at the wall positions (measurement positions) 1308.

The output/display unit 6 displays the measurement values calculated by the measurement unit 13 (step S410). They are displayed in a measurement value field 1202 of FIG. 13 and a measurement value field 1302 of FIG. 14. The output/display unit 6 may display the set regions of interest (the Doppler gates 1203, the M-mode beam line 1303, the waveform positions 1206, and the wall positions 1308) so that they are superimposed on the ultrasonic images.

According to the present embodiment, in order to obtain the image data of Doppler or the M mode, the regions of interest are set on the image data of the B mode. Moreover, the regions of interest including the predetermined measurement positions are set on the image data of the measurement values about the measurement items of Doppler or the M mode. More specifically, after the regions of interest for obtaining the image data of Doppler or the M mode are set in the image data of the B mode, the regions of interest for carrying out measurement of the measurement items can be set in the image data of Doppler or the M mode. As a result, a plurality of regions of interest can be set in various image data. Therefore, Doppler image data or M-mode image data at the position desired by the examiner is generated by setting the regions of interest in the B-mode image, and accuracy improvement of setting of the regions of interest and search time reduction can be achieved by setting the predetermined measurement positions (regions of interest) in accordance with the measurement item input by the examiner. Therefore, the medical image diagnostic device which reduces the operation load of setting of the regions of interest of the examiner can be provided.

Hereinabove, the first and second embodiments according to the present invention have been explained. However, the present invention is not limited thereto, and changes/modifications can be made within the range described in claims.

For example, in the first embodiment the reduction ratio (compression ratio) is changed to 1/1. However, in the process in which the reduction ratio (compression ratio) of the image data is gradually increased, measurement results of each reduction ratio (compression ratio) may be successively output, and the setting process of the region of interest may be terminated at the reduction ratio (compression ratio) that satisfies measurement accuracy, by using the output information of the measurement results. More specifically, in the first embodiment, the measurement unit 13 outputs the measurement result of the measurement item after the region of interest is set in the second search range; however, each measurement result of the measurement item may be separately output after the regions of interest are set in the first search range and the second search range.

Figure 15:
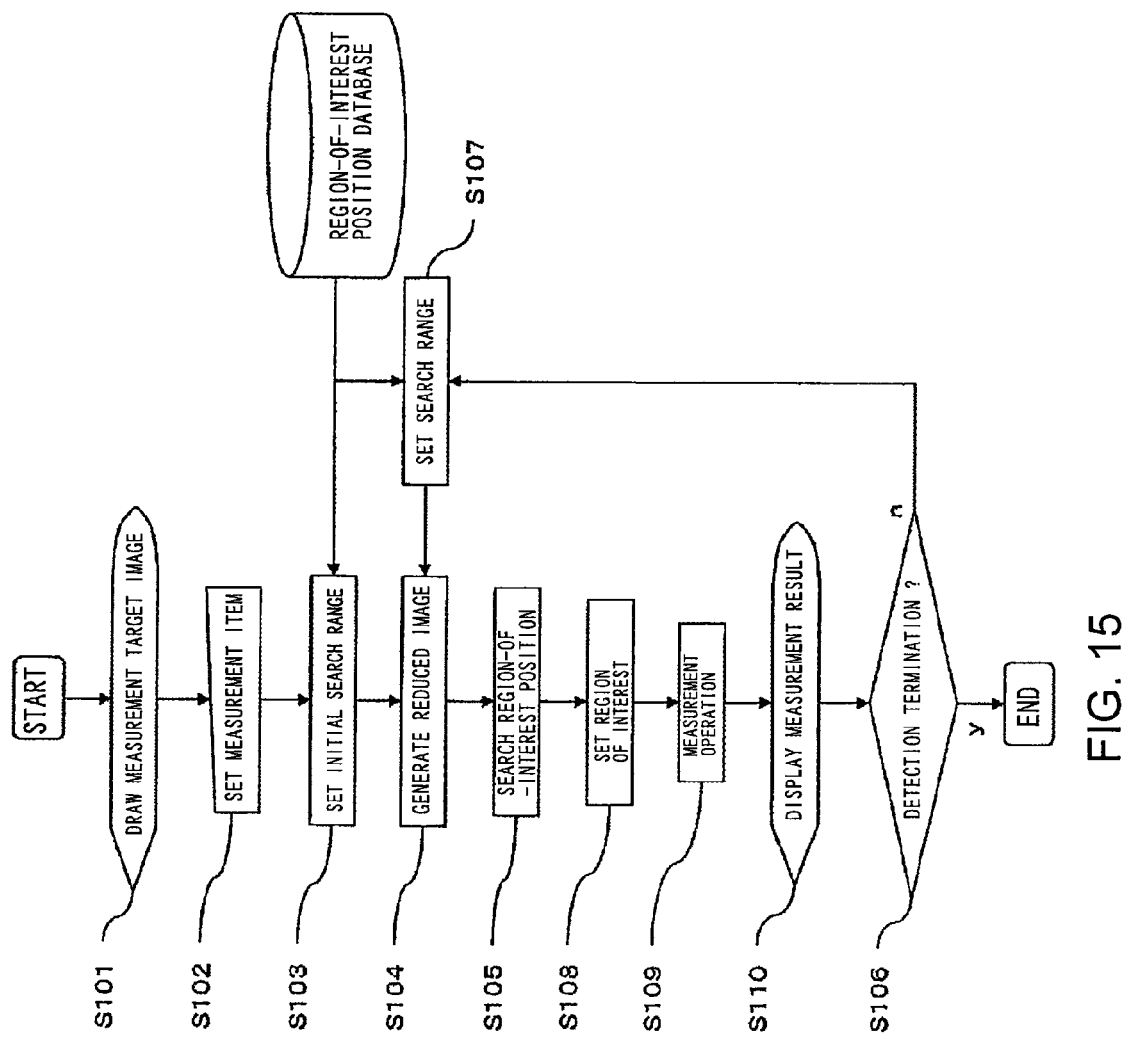
FIG. 15 is a flow chart of successively outputting a measurement result and judging whether to terminate setting of the region of interest in accordance with the measurement result.

FIG. 15 is a flow chart of successively outputting the measurement results and judging whether to terminate the setting of the region of interest in accordance with the measurement results. Compared with the flow chart of FIG. 2, step S106 of judging whether to terminate the setting is executed after step S110 of displaying the measurement result. More specifically, the measurement unit 13 outputs the measurement results of the measurement items after the regions of interest are set in the first search range and the second search range. By using the regions of interest set at a predetermined reduction ratio, the measurement unit 13 executes measurement, and the output/display unit 6 displays the measurement result. If this measurement result is appropriate, the measurement is terminated. If the measurement result is not appropriate, the process returns to step S107, and setting of a region of interest is carried out at a next reduction ratio (compression ratio). The judgment of whether the measurement result is appropriate may be carried out by checking the measurement value by the examiner, may be carried out by comparison with an appropriate value (threshold value) of a measurement result input by the input unit 7, or may be carried out by comparison with an appropriate value (threshold value) of the measurement result stored in the storage unit 5. Alternatively, whether it is getting closer to the appropriate value (threshold value) may be judged in order to terminate the setting process when it gets the closest to the appropriate value (threshold value). The region-of-interest setting unit 11 terminates setting of the region of interest based on the appropriate value of the measurement result.

As a result, if it is judged that an appropriate measurement value can be measured even before the reduction ratio (compression ratio) reaches 1/1, the setting process of the region of interest can be terminated. Therefore, while ensuring appropriate measurement precision, accuracy improvement of the setting of the region of interest and search time reduction can be achieved.

Moreover, a method for extracting the contour of a living-body tissue may be used. By setting the region of interest by using the contour extracting method and searching in detail the periphery of the set position thereof, the set precision of the region of interest can be increased. For example, by using a method for extracting the contour of the endocardium of the heart, a region of interest including the annulus and the cardiac apex part (characteristic parts) is set.

Figure 16:
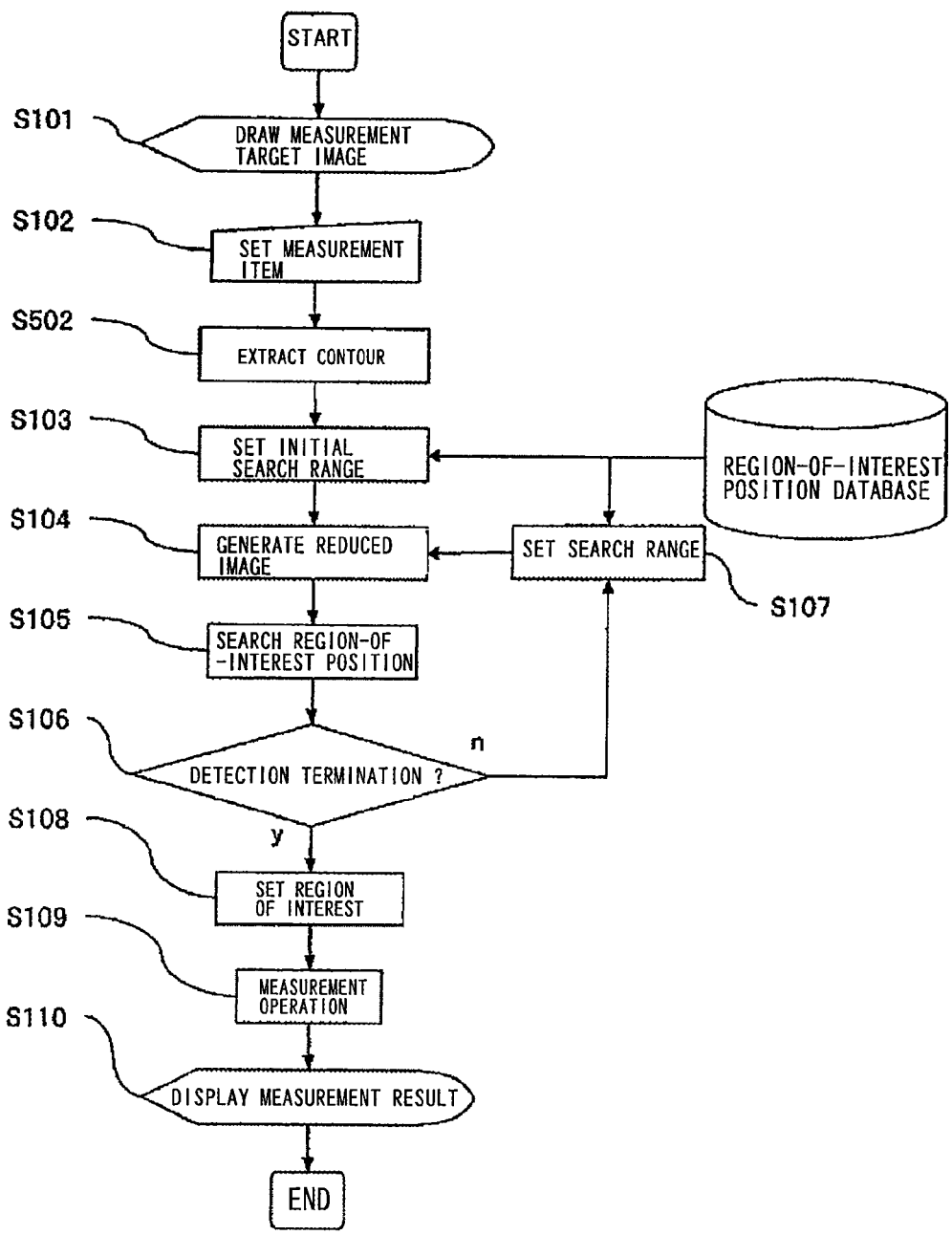
FIG. 16 is a flow chart explaining setting of a region of interest using a contour extracting method.

FIG. 16 is a flow chart explaining setting of a region of interest using a contour extracting method. As shown in FIG. 16, compared with the first embodiment, step S502 of carrying out a contour extracting process is added. The contour extracting process is desired to obtain a contour that has a limitation on the shape thereof such as a dynamic contour model. The contour unique to the left ventricle can be extracted by the limitation by a model capturing characteristics of the contour shape of the left ventricle, and a correct position relation between the annulus part and the cardiac apex part can be set. This model may be stored in the storage unit 5 and may be referenced upon contour extraction.

Figure 17:
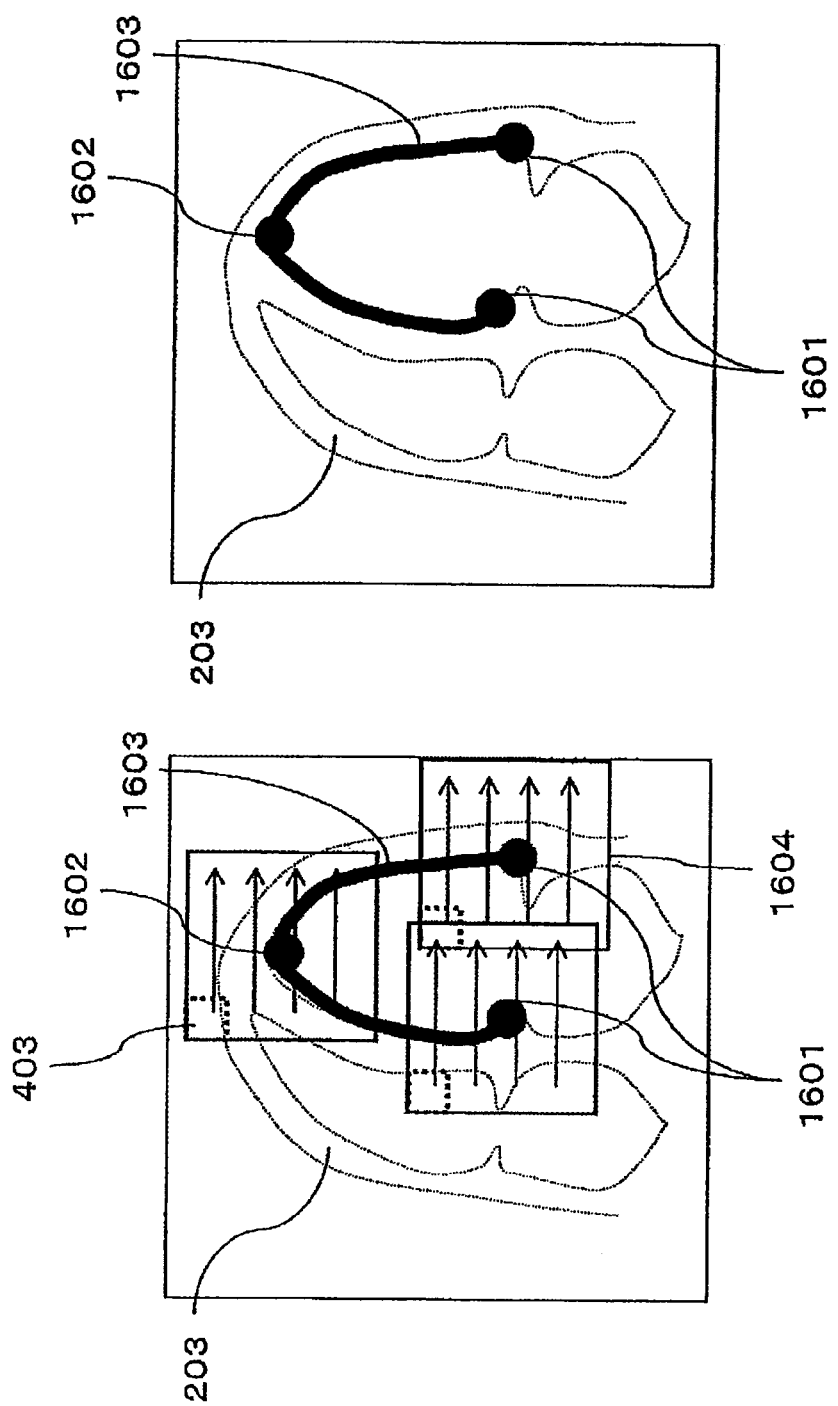
FIG. 17 shows drawings showing extracting a contour by a search-range setting unit in a contour extracting process and setting a search range by the search-range setting unit.

The search-range setting unit 9 carries out the contour extracting process (step S502). As shown in FIG. 17, in step S502 of carrying out the contour extracting process, the search-range setting unit 9 extracts a contour 1603. Even if precision is not high, the extracted contour 1603 is only required to be extracted so that the contour line fits the endocardium in a state in which the position relation of annulus parts 1601 and a cardiac apex part 1602 is maintained.

Then, the search-range setting unit 9 sets search ranges 1604 (step S107). The search-range setting unit 9 sets the search ranges 1604 while using the coordinate values (reference coordinates) of the annulus parts 1601 and the cardiac apex part 1602, which have been set in the contour extracting process, as the centers thereof. The search ranges 1604 may be set by using the past sample data of the region-of-interest database 12 as well as the first embodiment. Since the positions of the annulus parts 1601 and the cardiac apex part 1602 are set in the contour extracting process, the range of the search range 1604 may be set so as to be narrower than the standard deviation of the sample data.

The region-of-interest setting unit 8 sets a region of interest for measurement by the measurement unit 13 (step S108). In this case, the region of interest is the contour (line) 1603. Since the positions of the annulus parts 1601 and the cardiac apex part 1602 have been set in the processes before step S108, the contour 1603 is extracted so as to pass through the three points including the two annulus parts and the single cardiac apex part.

As a result, since the positions of the annulus parts 1601 and the cardiac apex part 1602 are set in the contour extracting process, even if the contour extracting process is not highly precise, the search range 1604 can be narrowly adjusted by using the set positions of the annulus parts 1601 and the cardiac apex part 1602 while maintaining the position relation between the annulus parts 1601 and the cardiac apex part 1602, and accuracy of setting the annulus parts 1601 and the cardiac apex part 1602 is also improved. Therefore, since the search range 1604 can be narrowly set, reduction of setting operation time can be realized together with improvement of setting precision.

Hereinabove, the embodiments according to the present invention have been explained. However, the present invention is not limited thereto, and changes/modifications can be made within the range described in the claims.

In the first and second embodiments, measurement of the heart in the ultrasonic diagnostic devices has been explained as examples. However, the present invention can be similarly applied also to other diagnostic devices and living-body tissues.

At least one of a tomographic image, an elasticity image, and a measurement-value image of a subject is required to be the image data. Examples of the medical image include X-ray images, CT, MRI, ultrasonic images (US), and angiography (angiographic picture). Thus, the image capturing unit 20 is, for example, an X-ray-image capturing device, an X-ray CT device, or an MRI device.

INDUSTRIAL APPLICABILITY

The medical image diagnostic devices according to the present invention can achieve accuracy improvement of setting of the region of interest and search time reduction by setting the search ranges by using the compressed data and setting the region of interest, for example, by template matching. Therefore, there is an advantage of provision of a medical image diagnostic devices which reduce the operation load on the examiner of setting the region of interest. The devices are useful as medical image diagnostic devices which set the region of interest including the characteristic part or the measurement position.

REFERENCE SIGNS LIST 1 ultrasonic diagnostic device, 2 probe, 3 ultrasonic-signal generating unit, 4 ultrasonic-image generating unit, 5 storage unit, 6 output/display unit, 7 input unit, 8 region-of-interest setting unit, 9 search-range setting unit, 10 image reducing unit (image-data compression unit), 11 region-of-interest setting unit, 12 region-of-interest database, 13 measurement unit, 14 control unit, 20 image capturing unit, 203 the heart

The invention claimed is:

1. A medical image diagnostic device comprising:
an image capturing unit that captures a medical image of a subject; and
a processor including:
an image-data compression unit configured to use image data of the captured medical image of the subject as uncompressed image data and to generate compressed image data by compression based on a plurality of pixels of the uncompressed image data;
a search-range setting unit configured to set a search range of the compressed image data and configured to set a search range of the uncompressed image data; and
a region-of-interest setting unit configured to set a region of interest in the medical image based on the search range of the uncompressed image data and the search range of the compressed image data.

2. The medical image diagnostic device according to claim 1, wherein the search-range setting unit is configured to set the search range before the compression in a size equal to the search range after the compression.

3. The medical image diagnostic device according to claim 2, wherein the search-range setting unit is configured to set a reference coordinate, which is a coordinate value of a characteristic part set in a contour extracting process, as a center of the search range.

4. The medical image diagnostic device according to claim 3, wherein the search-range setting unit is configured to use the reference coordinate, which is an average of a coordinate value of a region of interest based on sample data, as a center and sets a standard deviation of the coordinate value of the region of interest as the search range.

5. The medical image diagnostic device according to claim 1,
further comprising a reference-coordinate storage unit that stores a reference coordinate serving as a reference of the position of the region of interest, and
wherein the search-range setting unit is configured to set the search range based on the reference coordinate.

6. The medical image diagnostic device according to claim 1,
further comprising a reference-coordinate storage unit that stores a reference coordinate serving as a reference of the position of the region of interest, and
wherein the search-range setting unit is configured to set the search range based on a coordinate difference between a coordinate of the set region of interest and the reference coordinate.

7. The medical image diagnostic device according to claim 6, wherein the search-range setting unit is configured to set the search range so that the coordinate difference is minimized.

8. The medical image diagnostic device according to claim 1, wherein when a first region of interest is set within a range overlapped with a plurality of the search ranges, based on the position of the first region of interest, the region-of-interest setting unit is configured to set a second region of interest within a limitation in part of the search range.

9. The medical image diagnostic device according to claim 8, wherein the region-of-interest setting unit is configured to:
set a region including a first annulus part of the heart as the first region of interest;
set a region including a second annulus part of the heart as the second region of interest;
if the first annulus part is positioned to the left side of the second annulus part, set the second annulus part within a limitation in the search range to the right side of the first annulus part; and,
if the first annulus part is positioned to the right side of the second annulus part, set the second annulus part within a limitation in the search range to the left side of the first annulus part.

10. The medical image diagnostic device according to claim 1, wherein the processor further includes a measurement unit configured to measure a measurement item in the set region of interest and configured to output a measurement result of the measurement item after the region of interest is set in at least one of the search range after the compression and the search range before the compression.

11. The medical image diagnostic device according to claim 10, wherein the region-of-interest setting unit is configured to terminate setting of the region of interest based on an appropriate value of the measurement result.

12. The medical image diagnostic device according to claim 1, wherein
the image data compression unit is configured to generate the compressed image data at a plurality of different compression ratios;
the search-range setting unit is configured to set search ranges respectively for the plurality of pieces of generated compressed image data; and the region-of-interest setting unit is configured to set the region of interest in the medical image based on the search ranges of the plurality of pieces of generated compressed image data.

13. The medical image diagnostic device according to claim 12, wherein the region-of-interest setting unit is configured to arbitrarily select the search range of the plurality of pieces of generated compressed image data and to set the region of interest in the medical image based on the selected search range.

14. The medical image diagnostic device according to claim 12, wherein the region-of-interest setting unit is configured to form a plurality of levels in which the search ranges of the plurality of pieces of generated compressed image data are arranged in accordance with the compression ratios, arbitrarily selects a level from the formed levels, and sets the region of interest in the medical image based on the search range of the selected level.

15. A region-of-interest setting method of a medical image diagnostic device including:
    capturing a medical image of a subject by an image capturing unit;
    using image data of the captured medical image of the subject as uncompressed image data and generating compressed image data by compression based on a plurality of pixels of the uncompressed image data by an image-data compression unit;
    setting a search range of the compressed image data and setting a search range of the uncompressed image data by the search-range setting unit; and
    setting a region of interest in the medical image based on the search range of the uncompressed image data and the search range of the compressed image data by a region-of-interest setting unit.

* * * * *